(12) United States Patent
Fogarty et al.

(10) Patent No.: US 9,186,251 B2
(45) Date of Patent: Nov. 17, 2015

(54) PUMP FOR AN IMPLANTABLE PENILE PROSTHESIS

(71) Applicant: Coloplast A/S, Humlebaek (DK)

(72) Inventors: Terence M. Fogarty, Hudson, WI (US); Robert A. Arp, Eden Prairie, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/561,222

(22) Filed: Dec. 5, 2014

(65) Prior Publication Data

US 2015/0087897 A1   Mar. 26, 2015

Related U.S. Application Data

(63) Continuation of application No. 14/106,864, filed on Dec. 16, 2013, now Pat. No. 8,932,204, which is a continuation of application No. 13/314,201, filed on Dec. 8, 2011, now Pat. No. 8,632,456, which is a continuation of application No. 11/613,148, filed on Dec. 19, 2006, now Pat. No. 8,167,788.

(60) Provisional application No. 60/752,211, filed on Dec. 19, 2005.

(51) Int. Cl.
*A61F 2/26* (2006.01)
*A61F 5/41* (2006.01)

(52) U.S. Cl.
CPC ... *A61F 2/26* (2013.01); *A61F 5/41* (2013.01); *A61F 2005/415* (2013.01)

(58) Field of Classification Search
CPC ........ A61F 2/26; A61F 5/41; A61F 2005/415
USPC ........ 600/29–32, 38–41; 623/11.11; 128/843, 128/DIG. 25
See application file for complete search history.

(56) References Cited

U.S. PATENT DOCUMENTS

| | | | | |
|---|---|---|---|---|
| 4,566,446 | A | * | 1/1986 | Fogarty ........................... 600/40 |
| 5,141,509 | A | * | 8/1992 | Burton et al. .................... 600/40 |
| 2004/0220447 | A1 | * | 11/2004 | Morningstar ................... 600/40 |

* cited by examiner

*Primary Examiner* — Samuel Gilbert
(74) *Attorney, Agent, or Firm* — Cotoplast Corp., Coloplast A/S; Nick Baumann

(57) ABSTRACT

A pump adapted to be attached between a reservoir and an inflatable penile implant of an implantable penile prosthesis includes a pump body connected between a pump bulb and tubing that is attachable to the reservoir and to the inflatable penile implant. An inlet valve and an exhaust valve are disposed within the pump body between the pump bulb and the tubing. A deflate valve is disposed within the pump body between the inlet valve and the tubing. The deflate valve includes a valve stem connected between a spring stabilizer and a valve surface. An aperture is formed to extend entirely through the deflate valve.

13 Claims, 21 Drawing Sheets

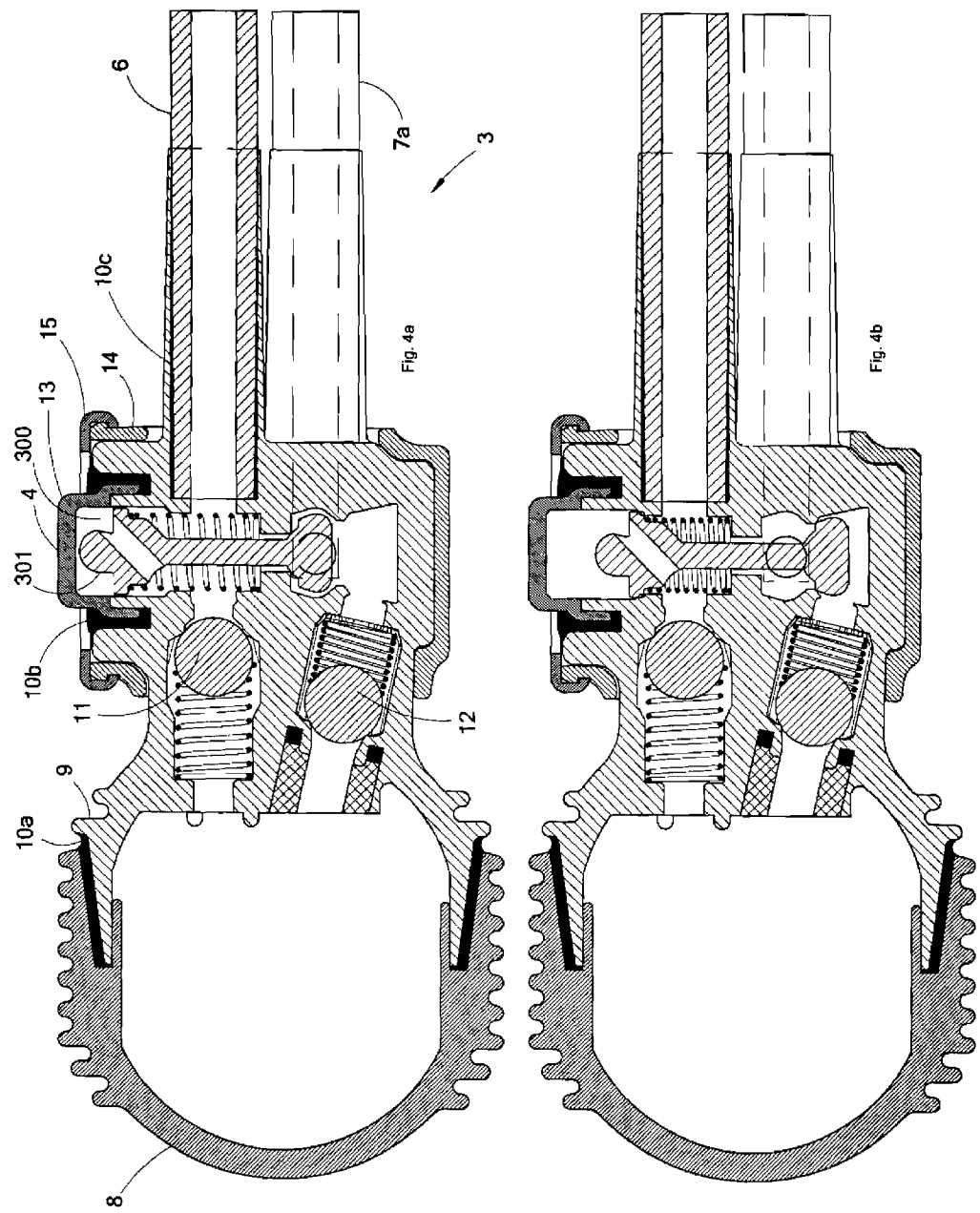

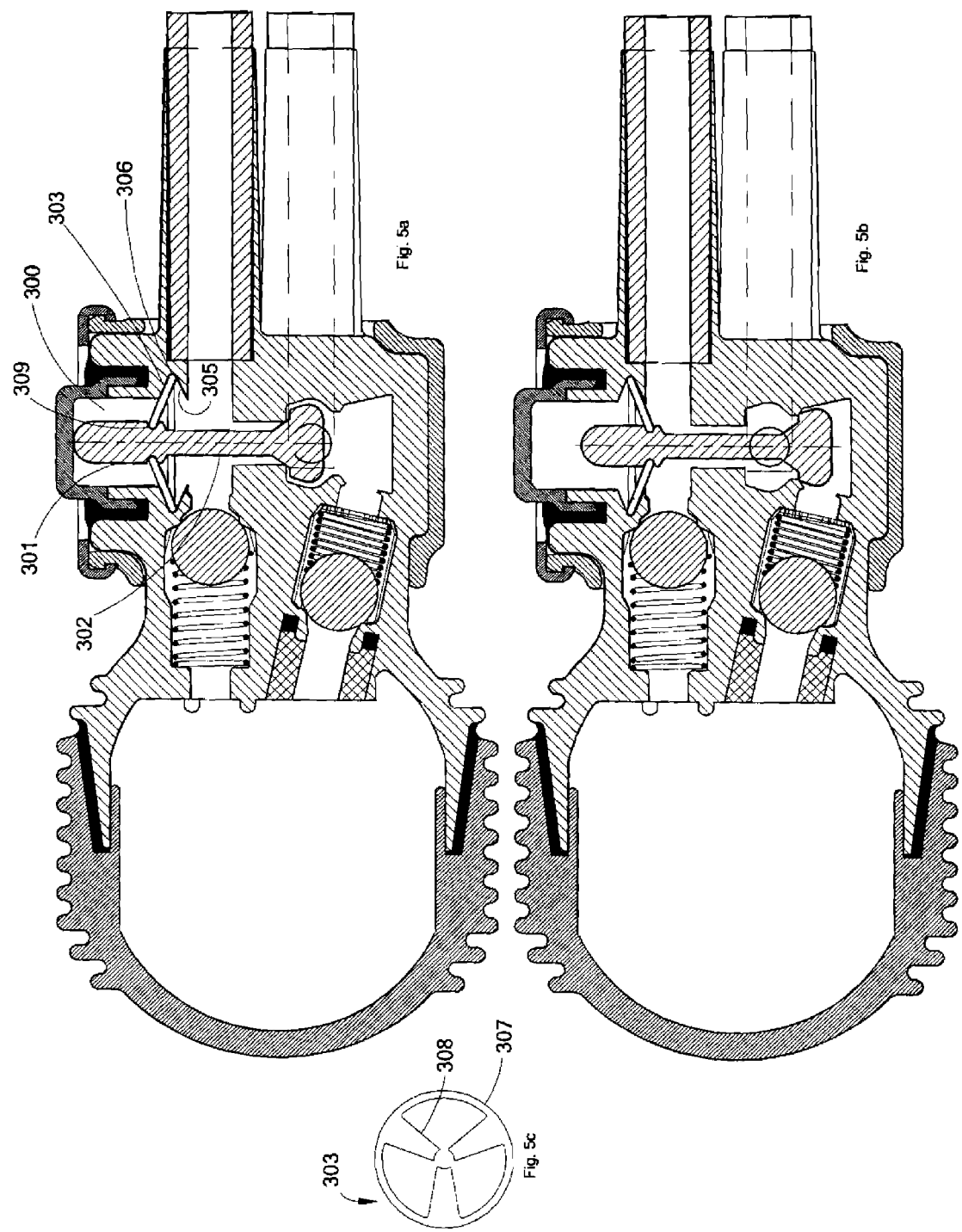

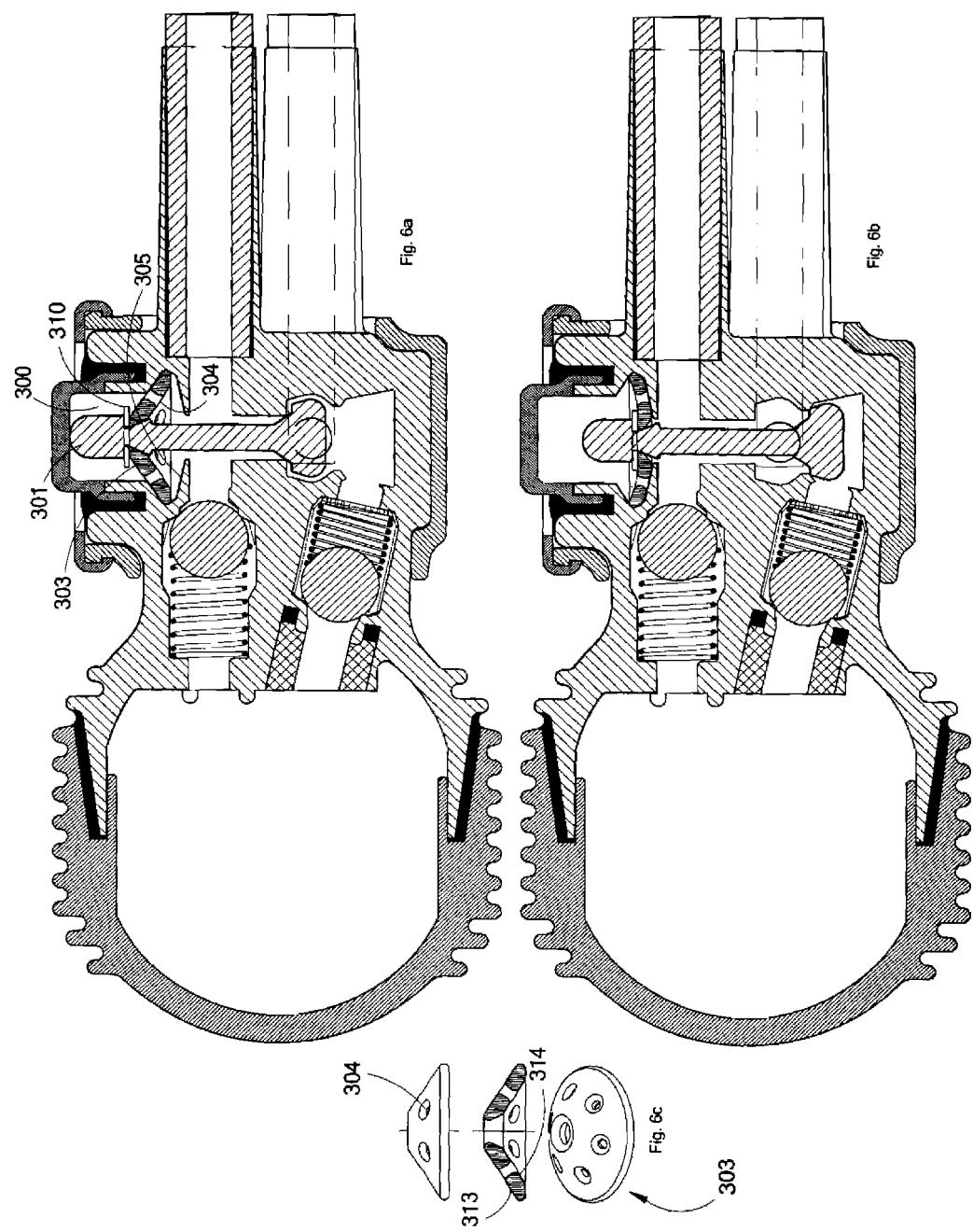

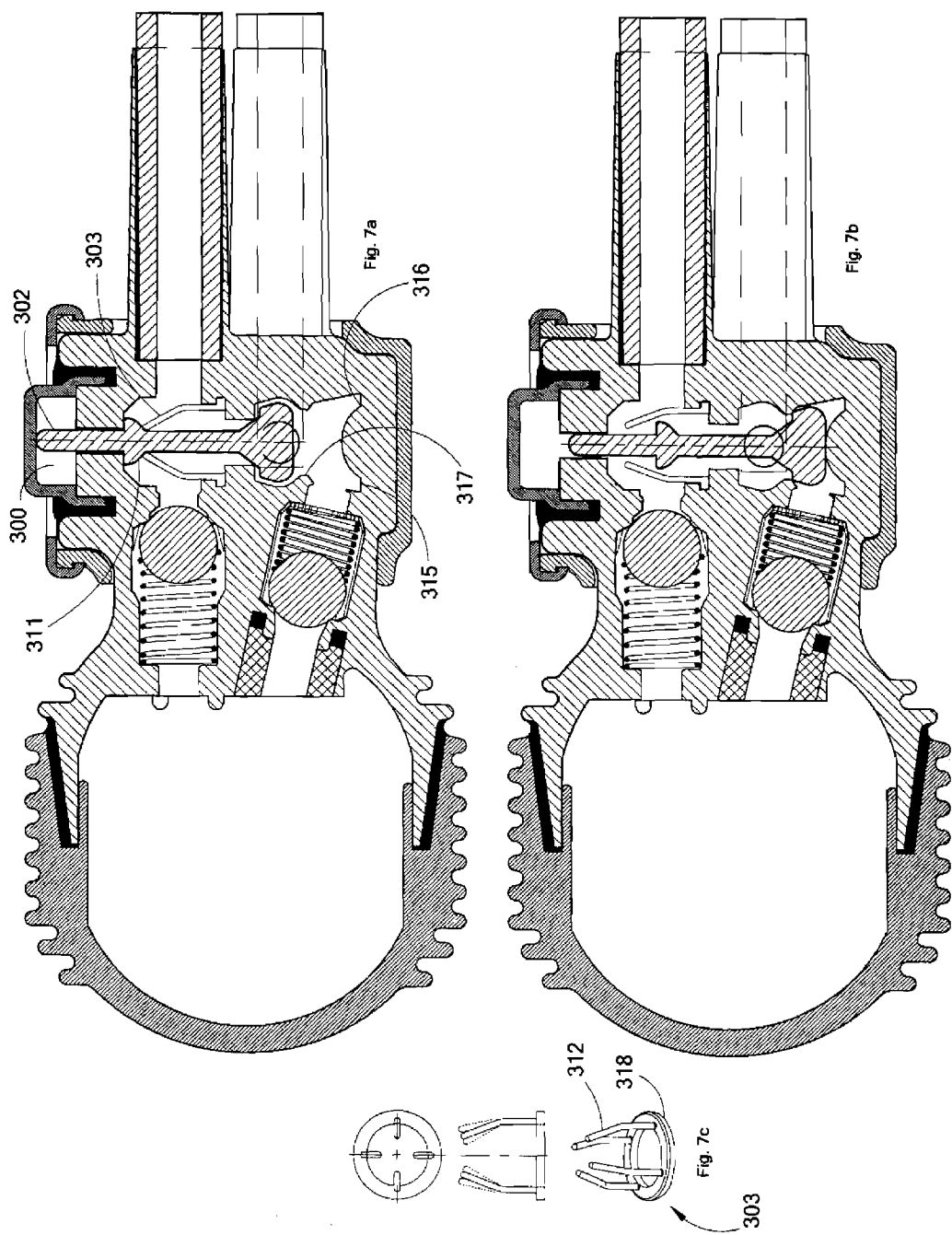

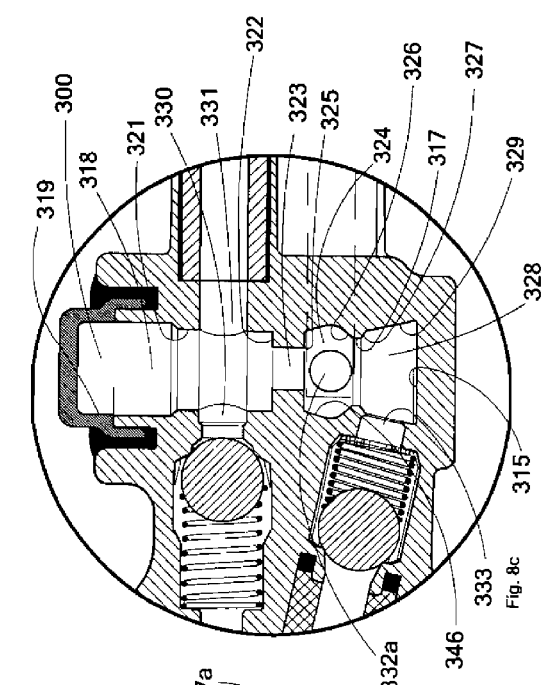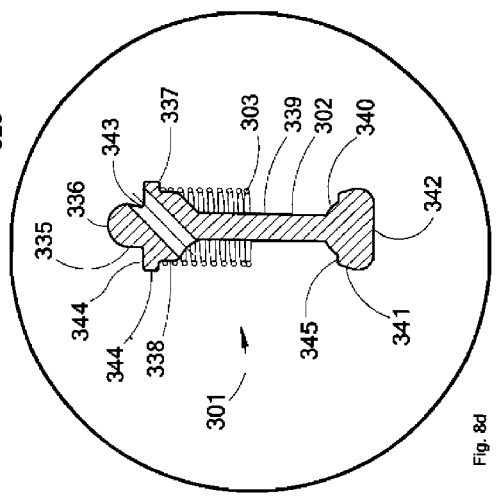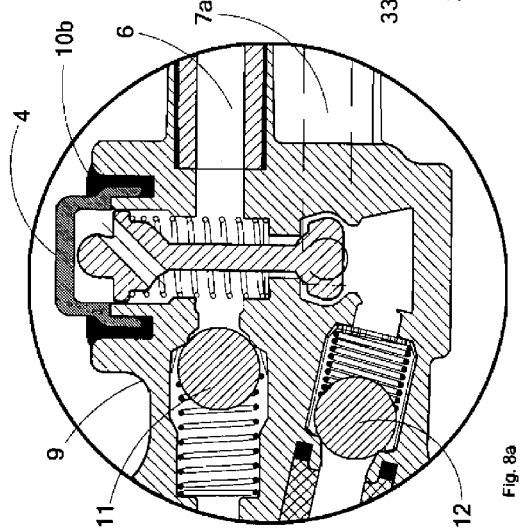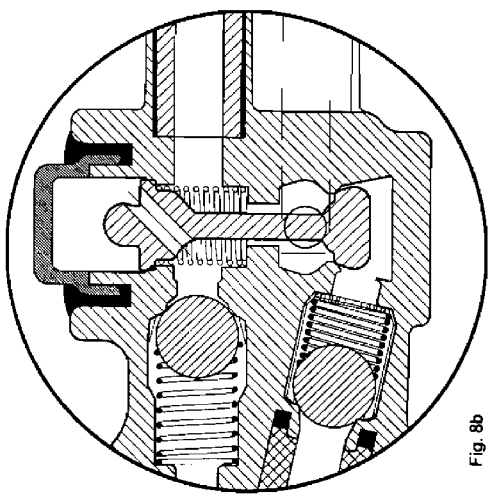

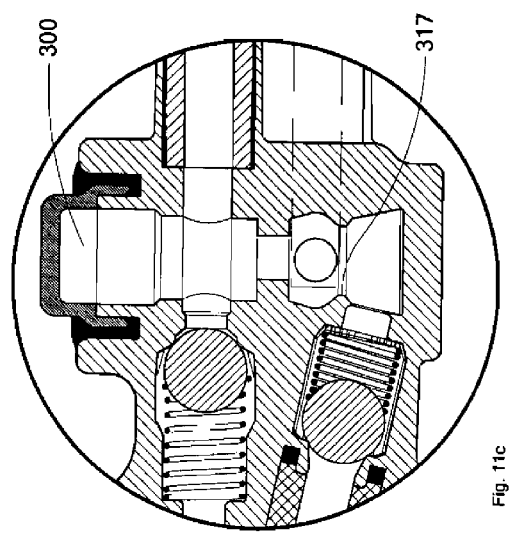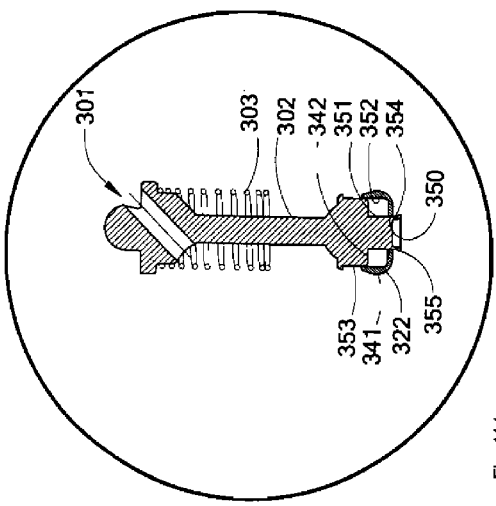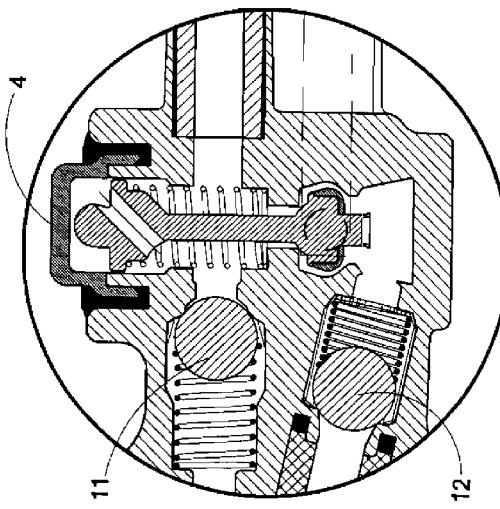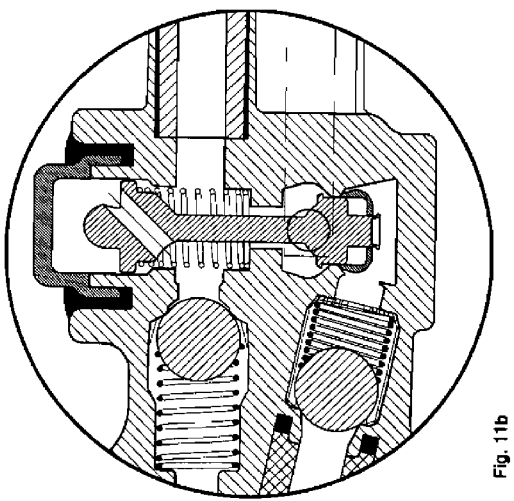

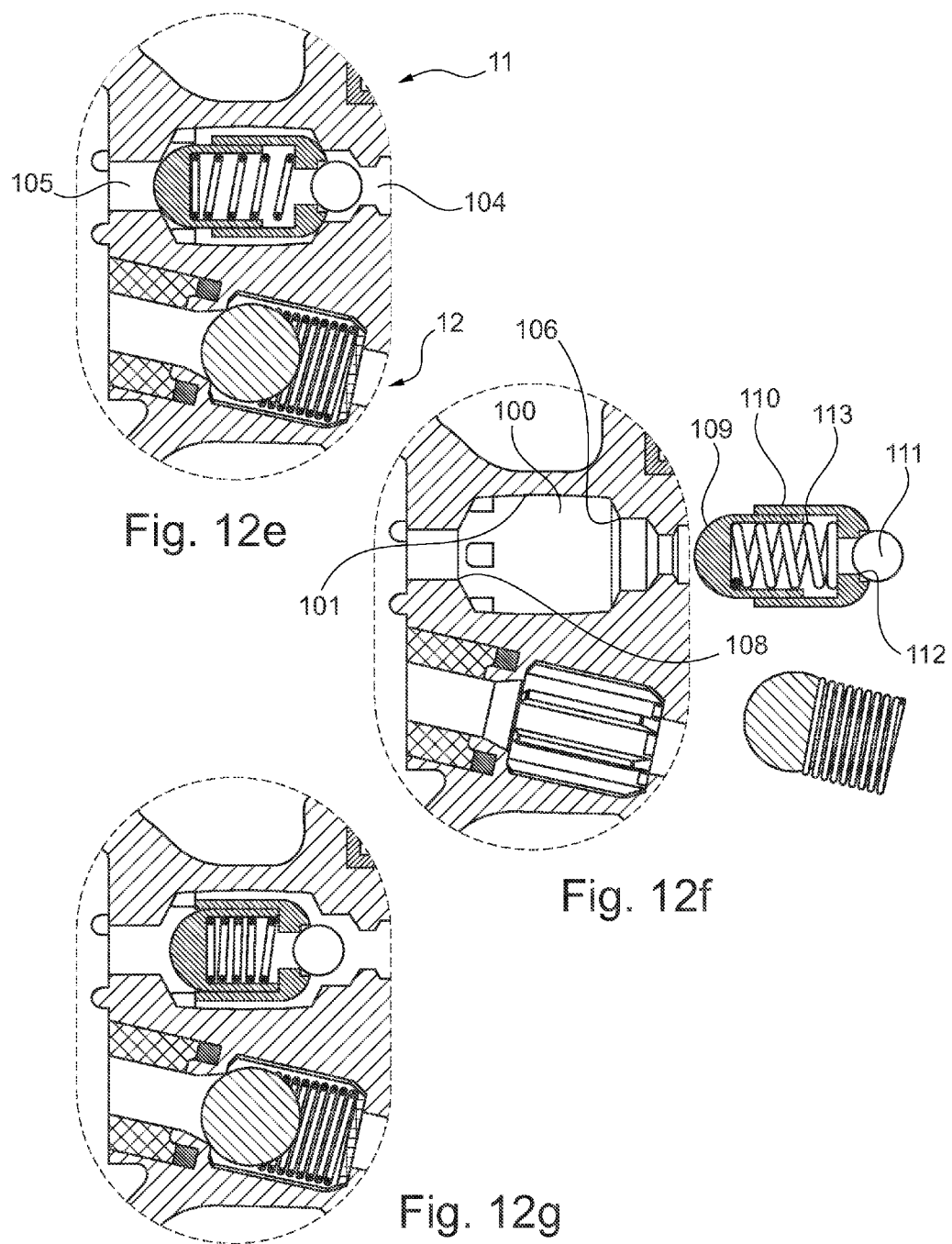

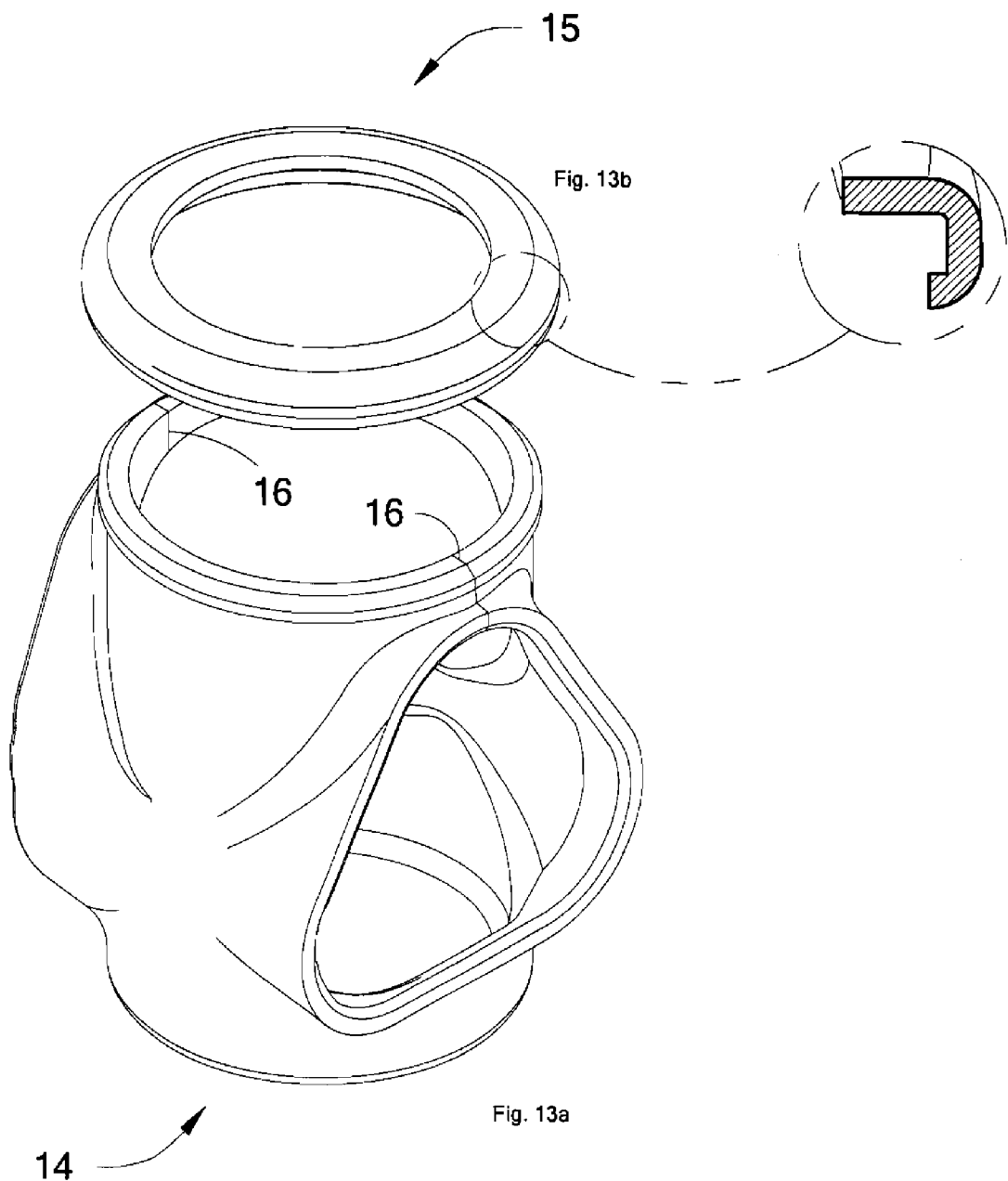

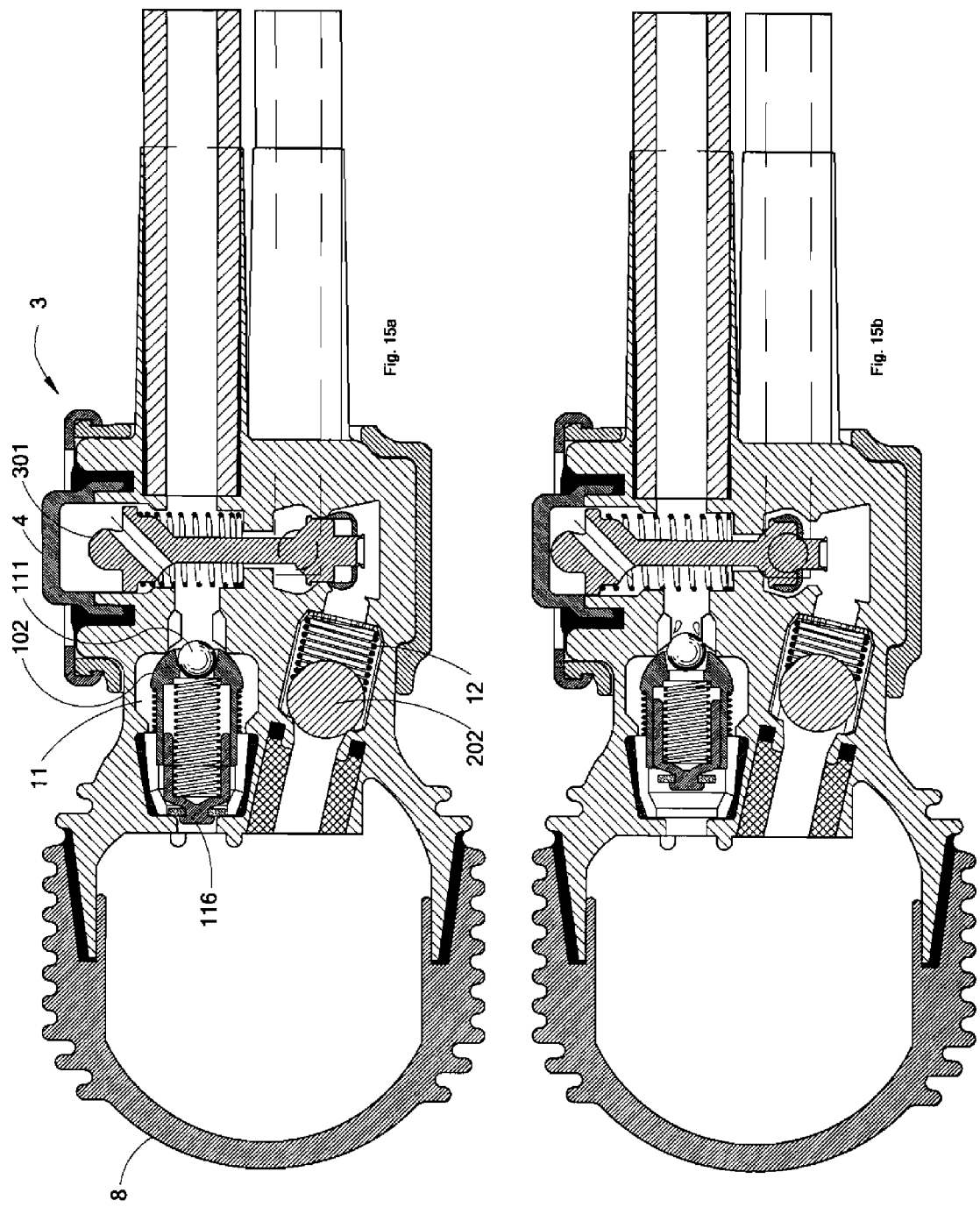

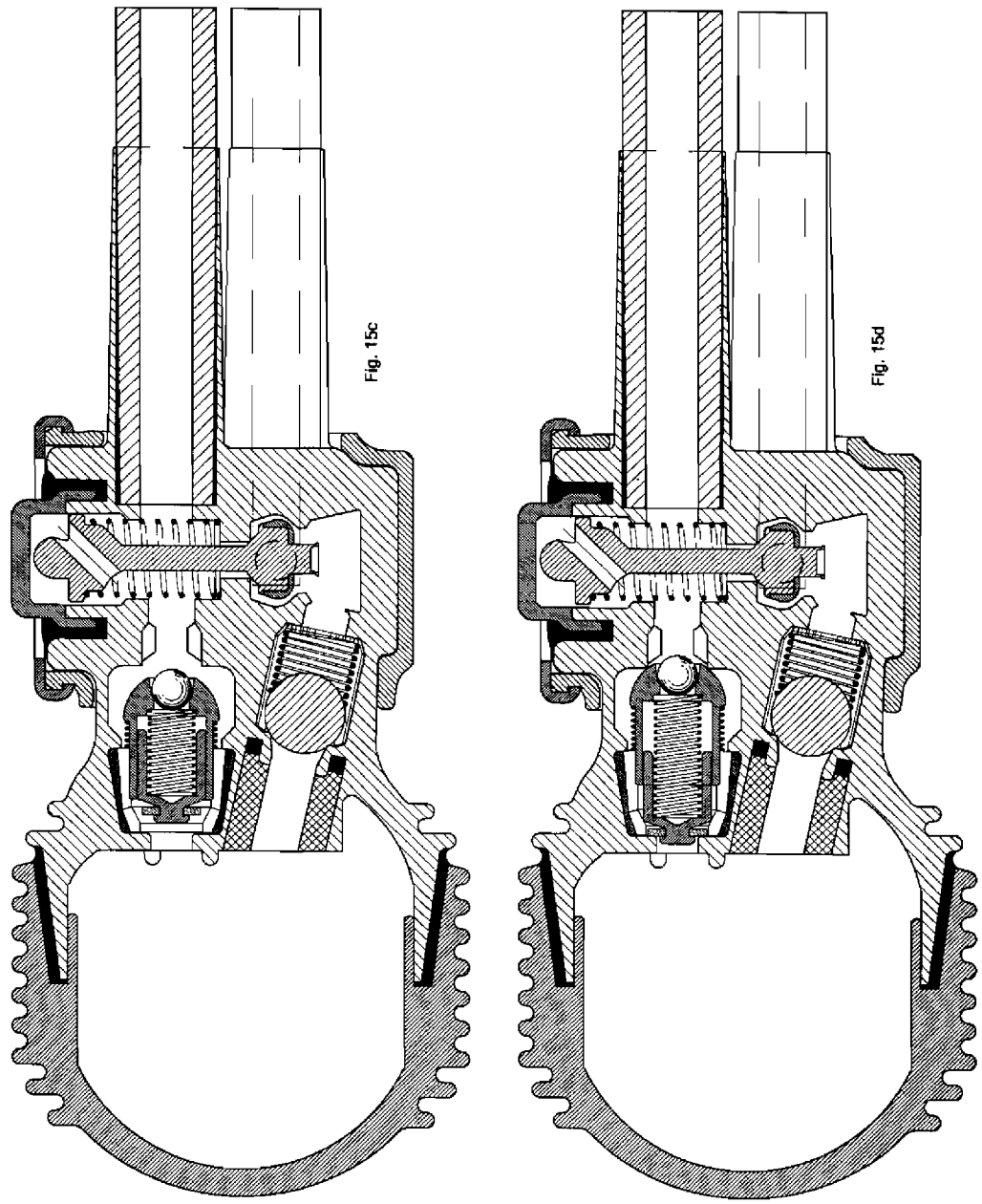

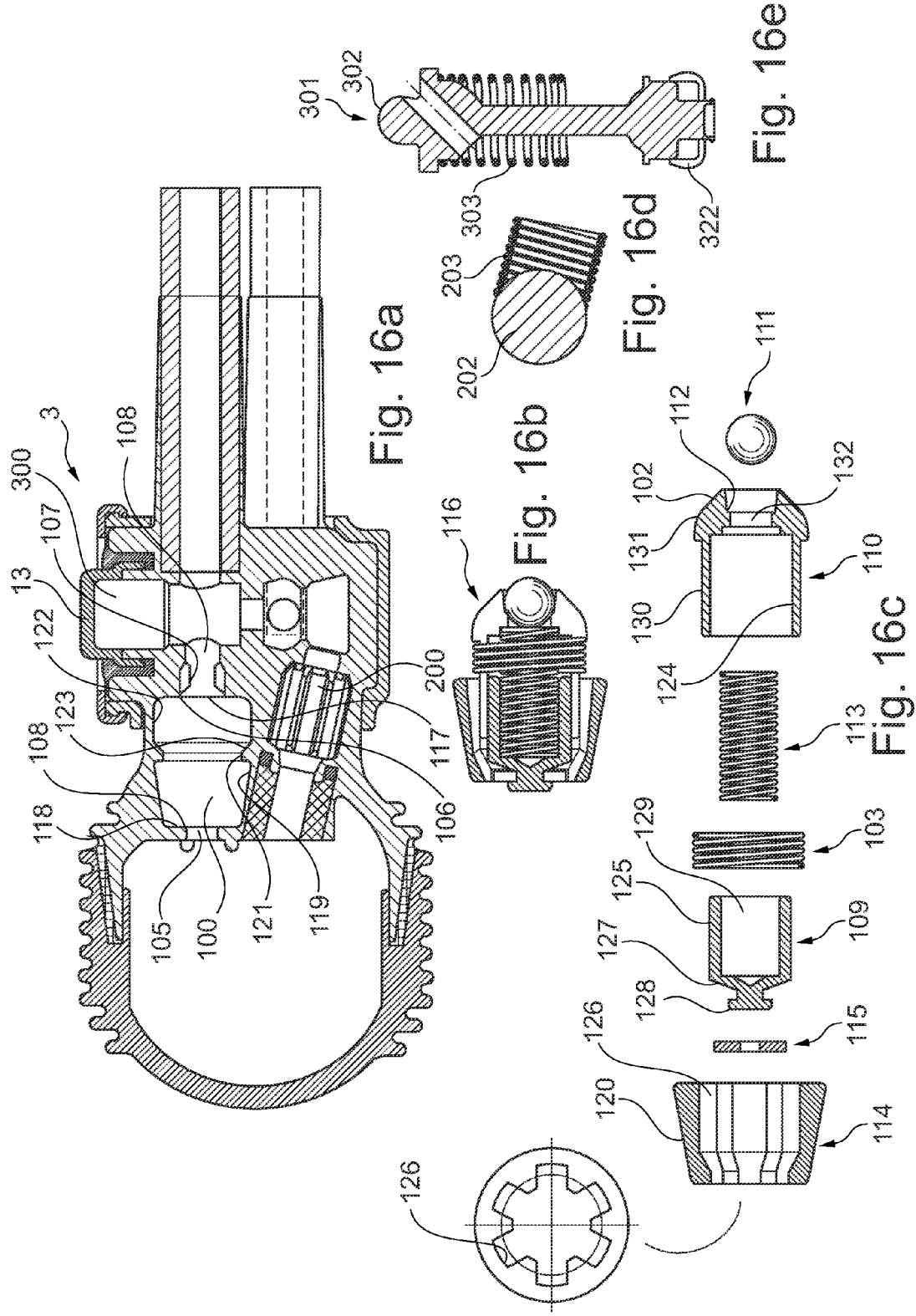

PUMP FOR AN IMPLANTABLE PENILE PROSTHESIS

TECHNICAL FIELD

In certain implementations, a pump for prostheses is described.

BACKGROUND

In certain devices, three piece inflatable penile prostheses (IPP's) consisted of an abdominal reservoir, a pair of inflatable penile cylinders and a scrotal pump to transfer fluid between the reservoir and cylinders. The pump may require repeated collapsing of the pump bulb to transfer fluid from the reservoir to the penile cylinders to achieve an erection. To deflate the cylinders and return the penis to the flaccid state, the pump valve mechanism can be squeezed until the desired amount of fluid is transferred.

SUMMARY

In certain implementations, a pump for a prosthesis is described.

One or more of the following advantages may be provided in certain implementations. First, a pump can be provided, which is not complex to manufacture. Second, a pump can be provided with a one-touch release that is easy for a patient to control. Third, an inflatable penile prosthesis (IPP) can include a larger bore tube or conduit between components of the IPP to reduce time needed to inflate and deflate the IPP. Fourth, a pump lockout valve for an IPP can be provided, which includes a reservoir and a pump bulb that, inter alia, opens to permit fluid flow from the reservoir to the pump bulb during pump bulb rebound.

In certain implementations, a pump with a one-touch release is provided for an inflatable penile prosthesis that in turn comprises a fluid reservoir, a pump bulb, a plurality of tubing, and at least one inflatable penile cylinder. The pump with a one-touch release includes a pump body, an inlet valve within the pump body, an exhaust valve within the pump body and in fluid communication with the inlet valve, and a deflate valve within the pump body and in fluid communication with the inlet valve and the exhaust valve. The deflate valve enables one-touch release by (i) providing a voluntarily-activated fluid bypass so that fluid from the at least one inflatable penile cylinder can return to the fluid reservoir through at least one of the plurality of tubing without sustained activation of the deflate valve, and (ii) closing upon subsequent inflation of the at least one inflatable penile cylinder when such inflation is initiated by squeezing the pump bulb so that fluid does not flow back to the fluid reservoir.

BRIEF DESCRIPTION OF THE DRAWINGS

FIG. 4a is a sectional view of the pump with a one-touch release shown in FIG. 3, with an illustrative deflate valve in an inflate mode.

FIG. 4b is a sectional view of the pump with the illustrative one-touch release shown in FIG. 3, with an illustrative deflate valve in a deflate mode.

FIG. 5a is a sectional view of the pump with the illustrative one-touch release shown in FIG. 3, utilizing an alternative rim and spoke spring in a deflate valve and depicting an inflate mode.

FIG. 5b is a sectional view of the pump with the illustrative one-touch release shown in FIG. 3, utilizing an alternative rim and spoke spring in a deflate valve and depicting a deflate mode.

FIG. 5c is an illustration of a rim and spoke spring depicted in FIGS. 5a-b.

FIG. 6a is a sectional view of the pump with a one-touch release shown in FIG. 3, utilizing an alternative elastomeric spring in an illustrative deflate valve and depicting an inflate mode.

FIG. 6b is a sectional view of the pump with the illustrative one-touch release shown in FIG. 3, utilizing an alternative elastomeric spring in a deflate valve and depicting a deflate mode.

FIG. 6c is an illustration of an elastomeric disc spring depicted in FIGS. 6a-b.

FIG. 7a is a sectional view of the pump with the illustrative one-touch release shown in FIG. 3, utilizing an alternative finger spring in a deflate valve and depicting an inflate mode.

FIG. 7b is a sectional view of the pump with the illustrative one-touch release shown in FIG. 3, utilizing an alternative finger spring in a deflate valve and depicting a deflate mode.

FIG. 7c is an illustration of a finger spring depicted in FIGS. 7a-b.

FIG. 8a is a sectional view of the pump with the illustrative one-touch release shown in FIG. 3, depicting a deflate valve in an inflate mode.

FIG. 8b is a sectional view of the pump with a one-touch release shown in FIG. 3, depicting a deflate valve in a deflate mode.

FIG. 8c is an illustration of the pump with the illustrative one-touch release depicted in FIGS. 8a-b with the deflate valve removed.

FIG. 8d is an illustration of the deflate valve of FIGS. 8a-b.

FIG. 11a is a sectional view of the pump with the illustrative one-touch release shown in FIG. 3, depicting an alternative articulated deflate valve in an inflate mode.

FIG. 11b is a sectional view of the pump with the illustrative one-touch release shown in FIG. 3, depicting an alternative articulated deflate valve in a deflate mode.

FIG. 11c is an illustration of the pump with the illustrative one-touch release depicted in FIGS. 11a-b, with the alternative articulated deflate valve removed.

FIG. 11d is an illustration of the alternative articulated deflate valve of FIGS. 11a-b.

FIG. 12e is a sectional view of a multi-functional inlet valve with a secondary valve seat, a spring loaded dashpot-type valve, and an exhaust valve, with the inlet valve being in a closed position.

FIG. 12f is an illustration of the valve assembly of FIG. 12e with the valve components removed therefrom.

FIG. 12g is an illustration of the valve assembly of FIG. 12e with the inlet valve being in an open position.

FIG. 13a is a magnified illustration of a clamshell-like girdle component of the pump with a one-touch release of FIG. 3.

FIG. 13b is an illustration of a snap ring component for locking together the clamshell-like girdle component of FIG. 13a.

FIG. 15a is a sectional view of the alternative embodiment of the pump with the illustrative one-touch release shown in FIG. 14, when a penis within which the device is implanted is flaccid and the reservoir is filled.

FIG. 15b is a sectional view of the alternative embodiment of the pump with the illustrative one-touch release shown in FIG. 14, when the pump bulb is squeezed and fluid flows into the cylinders.

FIG. 15c is a sectional view of the alternative embodiment of the pump with the illustrative one-touch release shown in FIG. 14, when the pump bulb is released and fluid is drawn into the pump bulb from the reservoir.

FIG. 15d is a sectional view of the alternative embodiment of the pump with the illustrative one-touch release shown in FIG. 14, when the penis is erect.

FIG. 16a is an illustration of the alternative embodiment of the pump with the illustrative one-touch release of FIGS. 15a-e, with valve components removed therefrom.

FIG. 16b is an illustration of a valve component shown in FIGS. 15a-e.

FIG. 16c is an exploded illustration of the valve component shown in FIG. 16b.

FIG. 16d is an illustration of another valve component shown in FIGS. 15a-e.

FIG. 16e is an illustration of another valve component shown in FIGS. 15a-e.

DETAILED DESCRIPTION OF ILLUSTRATIVE IMPLEMENTATIONS

Figure 1:
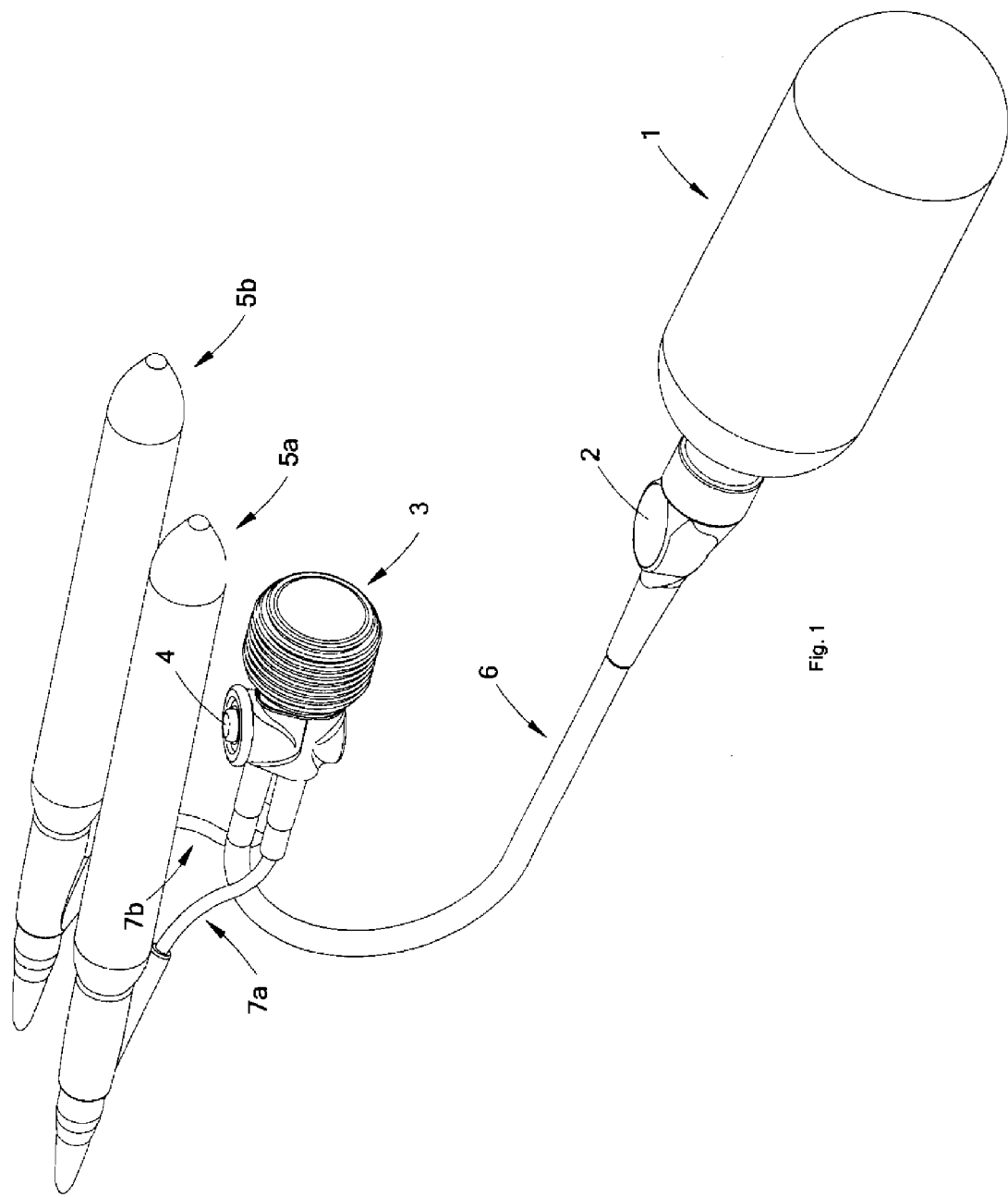
FIG. 1 is an illustration of an illustrative pump with a one-touch release that is utilized within an inflatable penile prosthesis (IPP), which includes (i) an illustrative larger bore tube or conduit between certain components therein and (ii) an illustrative pump lockout valve.

As used herein and throughout this application, the following terms are intended to have associated meanings and characteristics as noted.

"Inflatable Penile Prosthesis" (IPP) or "Inflatable Penile Prostheses" (IPPs): An IPP can be a unitary or multi-component (or, "multi-piece") device that is surgically implanted in a male patient to artificially achieve an erection for treatment of erectile dysfunction. Such IPPs operate hydraulically and may include (i) at least one penile cylinder, (ii) a fluid reservoir that is fluidly connected to the at least one penile cylinder, (iii) a pump to transfer fluid from the fluid reservoir to the at least one penile cylinder, (iv) and a deflation means for returning fluid from the at least one penile cylinder to the fluid reservoir.

"Pump": A pump can be used in an IPP to transfer fluid from a fluid reservoir to fill a penile cylinder and to thus pressurize the cylinder for rigidity. For example, in a unitary IPP, the pump can be located at a distal end of the prosthesis (i.e., nearest to the patient's glans penis). In a multi-component IPP, the pump may be implanted in the scrotum. Schematically, a pump typically includes (i) an elastomeric-type bulb that can be squeezed to transfer fluid between the fluid reservoir and the penile cylinder, and (ii) an inlet valve and an exhaust valve located between (a) the bulb and (b) an inlet tube and an exhaust tube, respectively. A pump can have valves biased for flow in one direction but arranged so that they can be opened to allow fluid to return through the valves in an opposite direction. A bypass valve may also be included as desired, for deflating the IPP without routing the fluid through the inlet and exhaust valves.

"Penile Cylinder": A penile cylinder typically includes an elongated, hollow, elastomeric-type chamber, defined by a cylinder wall, which can be inflated. It is to be particularly understood that as used herein and throughout this application, the singular term "penile cylinder" includes a plural meaning of one or more penile cylinders, when such interpretation is not in contextual conflict. The inflatable portion of the penile cylinder can be implanted in the pendulous portion of the penis which typically includes the hinge point of the penis. A relatively rigid cylinder base, along with one or more rear tip extenders for the penile cylinder, may be implanted in the patient's crus to stabilize the cylinder. The cylinder wall expands to engage the interior of the patient's corpus cavernosum. The penile cylinder may also be an elastic bladder that engages the patient's less elastic tunica albuginea to produce penile rigidity, similar to an inner tube in a tire.

"Reservoir": A reservoir (or "reservoir chamber") can be used for fluid storage in the IPP. In a unitary IPP, the reservoir may be located in various portions such as at a base of the penile cylinder (e.g., as shown in U.S. Pat. No. 4,360,010 to Finney), or inside an inflatable cylinder bladder or surrounding the inflatable bladder (e.g., as shown in U.S. Pat. No. 4,353,360 to Finney, et al.), or between a base of the penile cylinder and an inflatable portion of thereof (e.g., as shown in U.S. Pat. No. 4,364,379 to Finney). In multi-component IPPs the reservoir may be implanted subcutaneously (e.g., as shown in U.S. Pat. No. 4,559,931 to Fischell), or in the lower abdomen (e.g., as shown in U.S. Pat. No. 3,954,102 to Buuck), or in the scrotum or in the space of retzius as is also known. In still other multi-component IPPs, a pump and reservoir may be combined with the reservoir also acting as the pump bulb (e.g., as shown in U.S. Pat. No. 3,853,122 to Strauch, et al.).

"Inlet Valve": An inlet valve may be a normally closed valve located between a reservoir chamber and a pump bulb and can be biased to prevent flow back to the reservoir when the pump bulb is squeezed. A pressure differential caused by pump bulb rebound (as defined below) acts to open the valve to allow fluid to flow to the pump bulb.

"Exhaust Valve": An exhaust valve can be closed and biased to prevent flow from a penile cylinder to either or both a pump bulb and reservoir. The exhaust valve can be biased to stay closed in a range from about 0.5 psi to about 8.0 psi, to prevent fluid from flowing from the reservoir to a penile cylinder and thereby prevent unwanted autoinflation thereof (as described below).

"Deflate Valve": A deflate valve as described herein can include a bypass-type valve which provides an alternate fluid return channel between a reservoir and penile cylinder, and which bypasses the inlet valve and the exhaust valve.

"Inflate Mode" or "Inflation": In this condition, the deflate valve is closed.

"Deflate Mode" or "Deflation": In this condition, the deflate valve is open or activated.

"Device Inflation": In this condition there exists a voluntary transfer of fluid from the reservoir to the penile cylinder to cause an erection. This can be accomplished by compressing a reservoir or pump, or by repeatedly squeezing a pump bulb that is in fluid communication with the reservoir.

"Device Deflation": In this condition the penile cylinder returns from an erect state to a flaccid state. This can typically be accomplished by squeezing an elastomeric-type valve body to deform valve seats of both the inlet valve the exhaust valve to an open position, thereby allowing fluid to flow from the penile cylinder to the reservoir. If the penis itself is squeezed, increased intraluminal cylinder pressure may hasten the deflation process.

"Autoinflation": In this condition an involuntary inflation of the penile cylinder occurs. Autoinflation may result from intraluminal reservoir pressure that exceeds backpressure resistance of the exhaust valve. Autoinflation may also result from inadvertent pressure on the elastomeric-type valve body that opens the inlet valve and exhaust valve and allows fluid to flow therethrough.

"One-touch": An initial, nearly instantaneous activation rather than a sustained or prolonged activation. For example, a one-touch release, when utilized in a deflate valve, is actuated nearly instantaneously by a user without a need for sustained or prolonged pressure thereon. "Valve Backpressure": An amount of pressure that a normally closed valve will resist before opening in a flow direction. IPP exhaust valves typically are designed to provide desired valve backpressure resistance, to prevent unintentional fluid flow from the reservoir to the penile cylinder. In certain implementations, such valve backpressure resistance can exceed a maximum intraluminal pressure of the reservoir. As understood by those skilled in the IPP art, it may be impractical to have valve backpressure resistance exceed any reservoir intraluminal pressure because a force required to collapse the pump bulb and open the exhaust valve can also increase as valve backpressure resistance increases.

"Multi-functional Valve": A multi-functional valve is capable of providing at least two distinctly different functions.

"Rebound": A condition of a deformable vessel as it returns from a compressed state to an original, uncompressed state and fluid is urged to return thereinto due to a relatively sudden increase of volume or negative pressure within the vessel.

"Pump Lockout Valve": During inflation, a pump lockout valve opens to permit fluid flow from the reservoir to the pump bulb during pump bulb rebound; squeezing the pump bulb will also open the pump lockout valve but fluid flow back to the reservoir may be prevented by the inlet valve. During deflation, when the inlet and exhaust valves are open, fluid flows freely from the penile cylinders through the exhaust valve, the pump bulb, the pump lockout valve, the inlet valve, and to the reservoir. It is to be understood that a reservoir lockout valve (as defined below) may optionally be included in the aforedescribed fluid flow path.

"Reservoir Lockout Valve": During inflation, a reservoir lockout valve opens to permit fluid flow from the reservoir to the pump bulb during pump bulb rebound; rebound of the pump bulb can also open the reservoir lockout valve but fluid flow back to the reservoir can be prevented by the inlet valve. During deflation, when the inlet and exhaust valves are open, fluid flows freely from the penile cylinders through the exhaust valve, the pump bulb, the inlet valve, the reservoir lockout valve, and to the reservoir. It is to be understood that a pump lockout valve (as defined above) may optionally be included in the aforedescribed fluid flow path.

Turning, now, to FIG. 1, an exemplary IPP is depicted that includes a pump with a one-touch release. Therein, the IPP comprises a fluid reservoir 1 with lock-out valve 2, pump 3 with deflate valve 4, and a pair of penile cylinders 5a and 5b. Inlet tubing 6 provides a fluid conduit between reservoir 1 and pump 3, exhaust tubing 7a provides a fluid conduit between pump 3 and cylinder 5a, and exhaust tubing 7b provides a fluid conduit between pump 3 and cylinder 5b.

Figure 2:
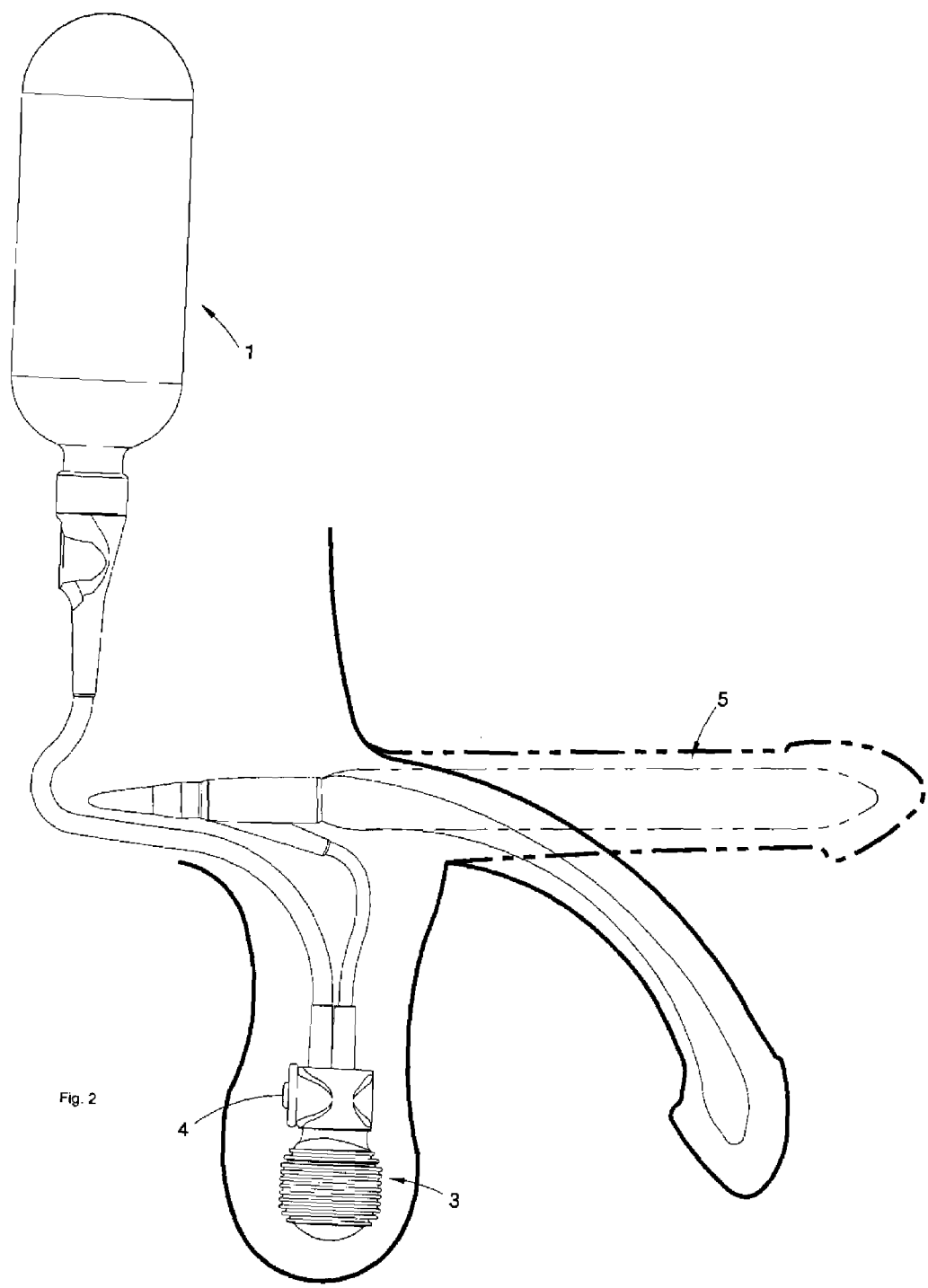
FIG. 2 is an illustration of a lower male abdomen implanted with the IPP of FIG. 1.

FIG. 2 is an illustration of a lower male abdomen implanted with the IPP of FIG. 1. Reservoir 1 can be implanted in the abdomen while pump 3 is implanted in the scrotum, and cylinders 5a-b are implanted in the Corpora Cavernosa of the penis. A pendant portion of the penis is depicted in both the flaccid and erect states.

Figure 3:
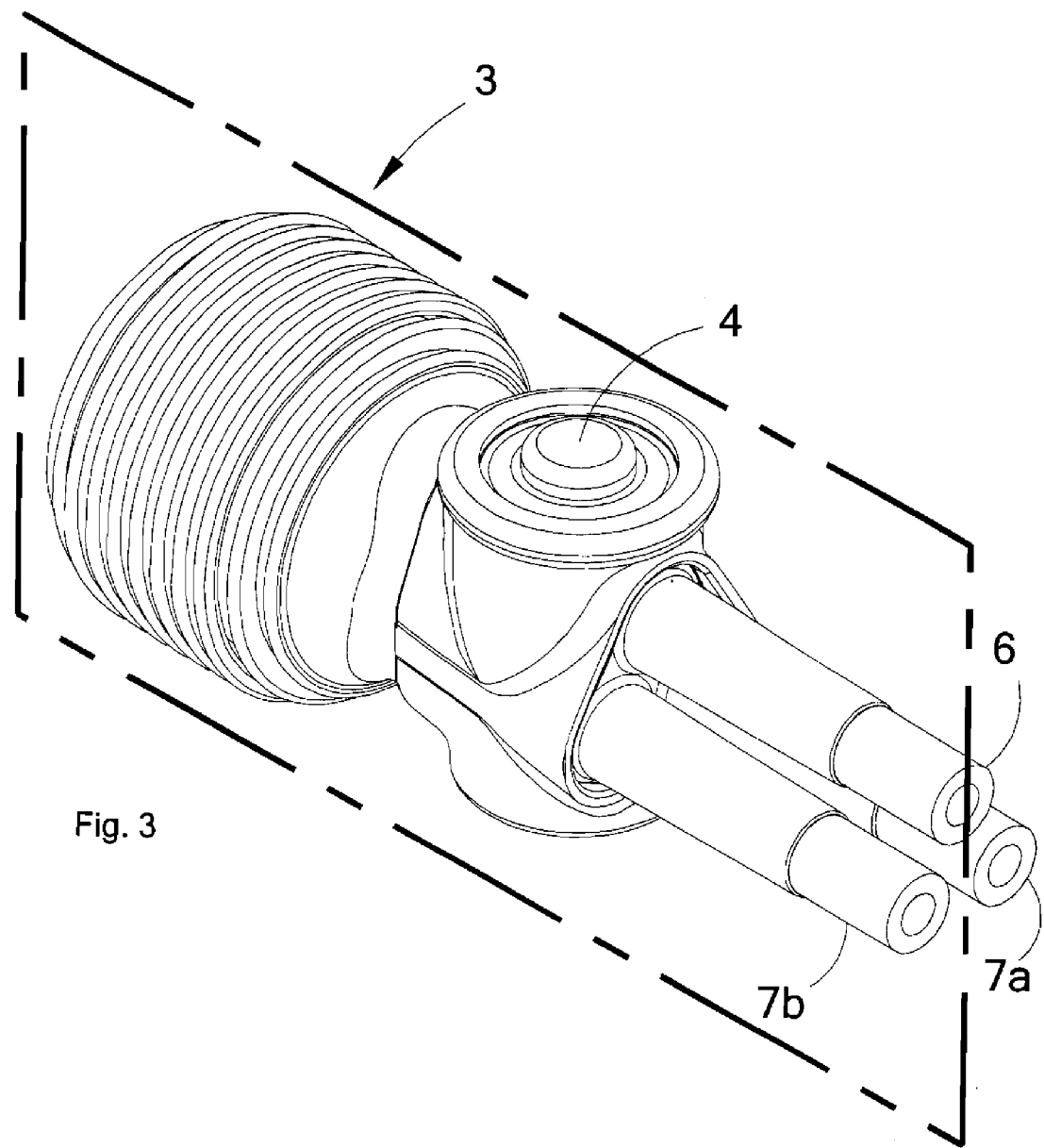
FIG. 3 is a magnified isometric view of the pump with an illustrative one-touch release as shown in FIGS. 1-2.

FIG. 3 is a magnified isometric view of the pump with a one-touch release as shown in FIGS. 1-2. Therein depicted is pump 3, deflate valve 4, and tubing 6 and 7a-b.

FIGS. 4a and 4b are sectional views of pump 3 with its deflate valve in an inflate mode and a deflate mode, respectively. In these drawings, pump 3 can include an elastomeric pump bulb 8 bonded to an elastomeric pump body 9 with adhesive 10a. Tubing 7a is bonded to pump body 9 with adhesive 10d, tubing 7b (not depicted in FIG. 4) is bonded to pump body 9 with adhesive 10e, and tubing 6 is similarly bonded to pump body 9. Pump 3 has three valves: an inlet valve 11, an exhaust valve 12, and a deflate valve 4. Deflate valve 4 includes a molded elastomeric chamber 300 that may be integrally molded with pump body 9. Deflate cap 13 is bonded to pump body 9 with adhesive 10b to close chamber 300 after valve sub-assembly 301 is installed. A girdle and a snap ring, as will be described, may be used to reinforce deflate valve 4 or to provide a rigid deflation zone.

FIG. 5a is a sectional view of pump 3, utilizing an alternative rim and spoke spring in a deflate valve and depicting an inflate mode. Therein, pump 3 can include elastomeric valve chamber 300 having a radial V-shaped recess 305 that supports rim and spoke spring 303 in inflate and deflate modes. A major diameter 306 of recess 305 cooperates with a rim 307 of spring 303 to provide a spring force to maintain valve 302 in inflate or deflate modes. Spokes 308 on spring 303 engage a groove 309 in valve 302 that causes rim 307 to distort as valve 302 is moved between inflate and deflate modes.

FIG. 5b is a sectional view of pump 3, utilizing alternative rim and spoke spring 303 in a deflate valve, and depicting a deflate mode.

FIG. 5c is an illustration of rim and spoke spring 303 as depicted in FIGS. 5a-b. Spring 303 may be fabricated from any suitable materials, such as metal or plastic with one or more spokes. In one embodiment, rim 307 is flexible and spokes 308 are rigid.

FIG. 6a is a sectional view of pump 3, utilizing an alternative elastomeric disc spring 303 in a deflate valve and depicting an inflate mode. Therein, pump 3 includes an elastomeric valve chamber 300 having a radial recess 305 that supports elastomeric disc spring 303 in inflate and deflate modes.

FIG. 6b is a sectional view of pump 3 utilizing alternative elastomeric disc spring 303, depicted as being in a deflate mode.

FIG. 6c is an illustration of elastomeric disc spring 303 depicted in FIGS. 6a-b. Elastomeric spring 303 is generally cone-shaped with apertures 304 through its frusto-conical surfaces 313 and 314 to permit fluid flow therethrough. Elastomeric disc spring 303 may be molded from materials, such as suitable medical grade silicone elastomer. Spring 303 is retained on valve 302 with split washer 310 that may be fabricated from any suitable materials, such as plastic or metal.

FIG. 7a is a sectional view of pump 3, utilizing an alternative finger spring 312 in deflate valve 302 and depicting an inflate mode. In this example, pump 3 includes elastomeric valve chamber 300 and finger spring 312, that engages a radial projection 311 on valve 302 to keep valve 302 in an inflate mode. With finger spring 312 there is no spring force acting on valve 302 to shift it from a deflate mode to an inflate mode. Instead, deflate chamber floor 315 has a convex projection 316 that keeps valve 302 against restriction ring 317.

FIG. 7b is a sectional view of pump 3, utilizing alternative finger spring 312 in deflate valve 302 and depicting a deflate mode.

FIG. 7c is an illustration of finger spring 303 as depicted in FIGS. 7a-b. Finger spring 303 has a base 318 and fingers 312 projecting from base 318. Finger spring 303 may be fabricated from any suitable metal or plastic and may include two or more fingers 312.

FIGS. 8a and 8b are sectional views of pump 3, depicting deflate valve 4 in an inflate mode and a deflate mode, respectively. In these drawings, specifically depicted are inlet valve 11, exhaust valve 12, and deflate valve 4.

FIG. 8c is an illustration of pump 3 as shown in FIGS. 8a-b, with valve assembly 301 of deflate valve 4 removed. Therein, deflate valve 4 includes deflate valve chamber 300 that is defined by a bonding of deflate cap 13 to pump body 9 with adhesive 10b. Deflate valve chamber 300 consists of valve guide compartment 318 with cylindrical surface 319, spring compartment 320 with cylindrical surface 321 and floor 315, fluid port 323, valve compartment 324 with valve seat 325 and axial surround 346, restriction ring 317 with frusto-conical ramps 326 and 327, and actuator compartment 328 with axial surround 329 and floor 315. Inlet valve entry port 330 and reservoir port 331 penetrate spring compartment 320. Cylinder ports 332a and 332b (not shown) penetrate valve compartment 324. Exhaust valve port 333 penetrates actuator chamber 328.

FIG. 8d is an illustration of valve assembly 301 of FIGS. 8a-b. Valve 302 has contact surface 336, gripping surface 335, guide surface 334, spring stop 337, spring stabilizer 338, valve stem 339, valve surface 340, ring engagement surface 341, valve shoulder 345 (which acts as a valve stop), and base 342. Aperture 343 penetrates valve guide 344, and allows fluid flow into deflate cap 13 so that rebound in the cap does not exert a negative force on valve guide 344 that might cause it to close prematurely. Spring 303 is shown as a compression coil spring and permits fluid flow between its coils. Gripping surface 335 is used in conjunction with a colleted tool to hold valve 302 while spring 303 is installed. Similarly colleted tools are used to grasp gripping surface 335 to inspect valve 302 and valve sub-assembly 301, and to place sub-assembly 301 into deflate valve chamber 300. In an inflate mode, spring 303 biases valve 302 against valve seat 325. In a deflate mode, deflate cap 13 is depressed to move valve 302 from valve compartment 324 to actuator compartment 328. Ring engagement surface 341 engages elastomeric restriction ring 317 to maintain valve 302 in the deflate mode. Initial pump bulb compression, during a subsequent device inflation, causes fluid flow from pump bulb 8 (as shown in FIG. 4a) through exhaust valve 12 and exhaust valve exit port 333 to pressurize actuator compartment 328, moving valve 302 through restriction ring 317. Thereafter, spring 303 returns valve 302 to the inflate mode.

In certain implementations, it is to be appreciated and understood that a restriction means, as exemplified above in restriction ring 317 cooperating with ring engagement surface 341, functions to maintain a valve in an open state until it is to be closed. Alternatively, a restriction means could be provided by way of a spring (e.g., in FIGS. 5a-c, spring 303 in cooperation with major diameter 306 of recess 305 and rim 307) that biases a valve in a selected open or closed state.

Figure 9C:
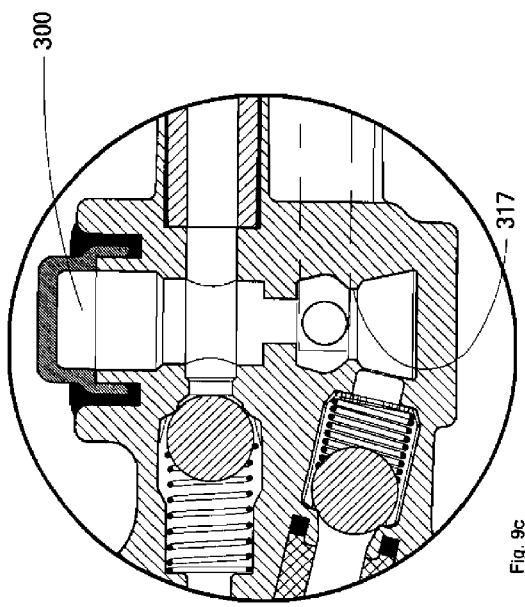
FIG. 9c is an illustration of the pump with the illustrative one-touch release depicted in FIGS. 9a-b, with the elongated ring engagement deflate valve removed.
Figure 9D:
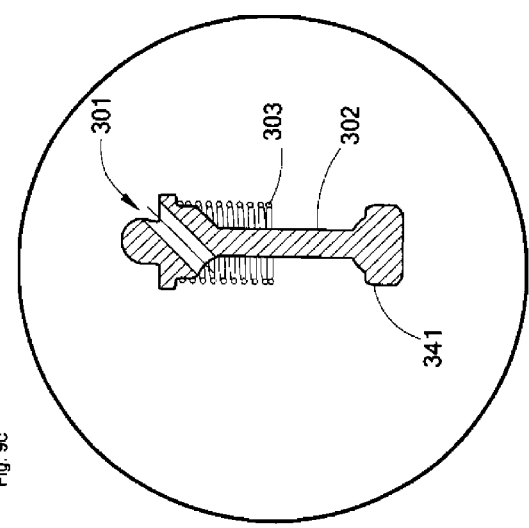
FIG. 9d is an illustration of the elongated ring engagement deflate valve of FIGS. 9a-b.
Figure 9A:
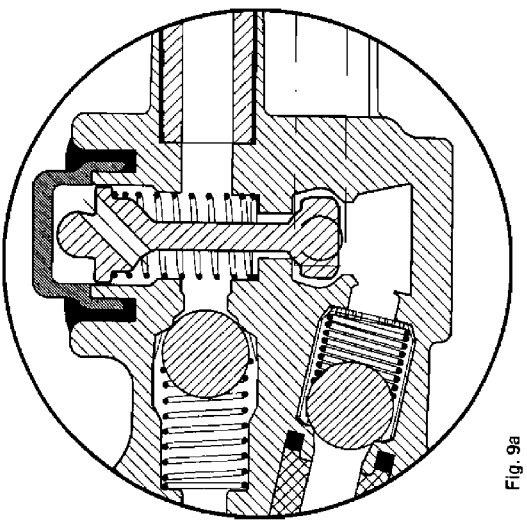
FIG. 9a is a sectional view of the pump with the illustrative one-touch release shown in FIG. 3, depicting an elongated ring engagement deflate valve in an inflate mode.
Figure 9B:
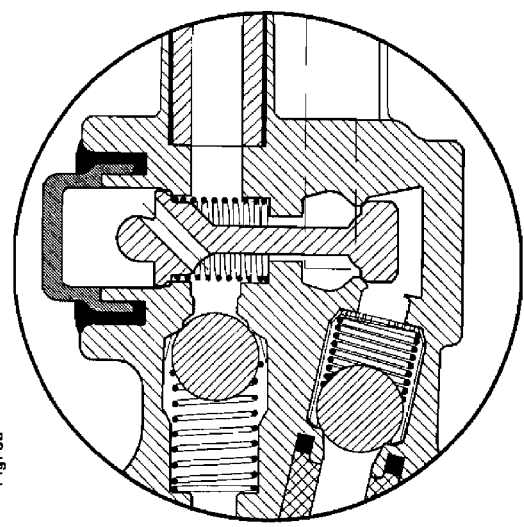
FIG. 9b is a sectional view of the pump with the illustrative one-touch release shown in FIG. 3, depicting an elongated ring engagement deflate valve in a deflate mode.

FIGS. 9a and 9b are sectional views of pump 3 shown in FIG. 3, depicting inlet valve 11, exhaust valve 12 and an elongated ring engagement deflate valve 4. FIG. 9a depicts elongated ring engagement deflate valve 4 in an inflate mode and FIG. 9b depicts valve 4 in a deflate mode.

FIG. 9c is an illustration of pump 3 depicted in FIGS. 9a-b, with elongated ring engagement deflate valve 4 removed. FIG. 9c is identical to FIG. 8c.

FIG. 9d is an illustration of elongated ring engagement deflate valve assembly 301 of FIGS. 9a-b. Assembly 301 includes valve 302 and spring 303. Valve assembly 301 shown in FIG. 9d is similar to that shown in FIG. 8d, except that upon close inspection of the drawings it will be discernable that in FIG. 9d valve 302 has an elongated ring engagement surface 341 as compared to surface 341 in FIG. 8d. In FIG. 9d, an apex of a radial projection is elongated parallel with an axial centerline of valve 302. During device deflation, deflate chamber 300 is pressurized and expands both radially and axially. Elongated ring engagement surface 341 of FIG. 9d then compensates for axial expansion of deflate chamber 300 and is retained in restriction ring 317 until a radial apex of ring engagement surface 341 passes through restriction ring 317.

Figure 10C:
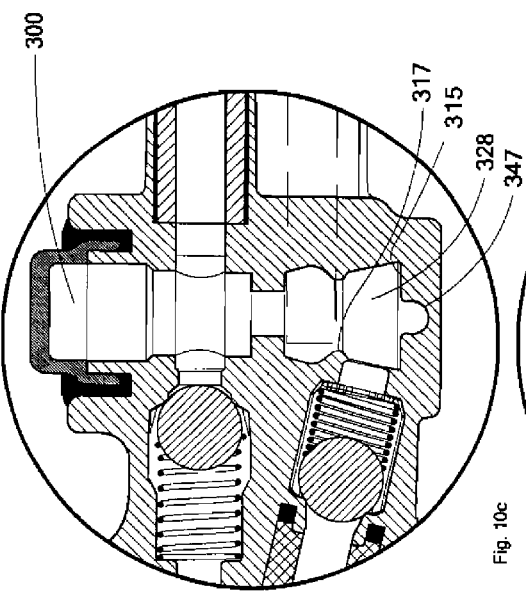
FIG. 10c is an illustration of the pump with the illustrative one-touch release depicted in FIGS. 10a-b, with the alternative ball and socket deflate valve removed.
Figure 10D:
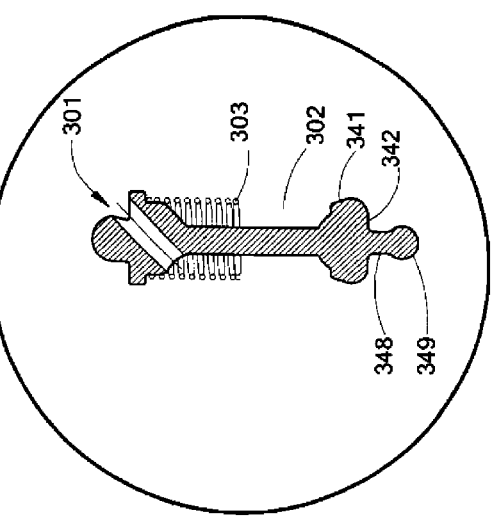
FIG. 10d is an illustration of the alternative ball and socket deflate valve of FIGS. 10a-b.
Figure 10A:
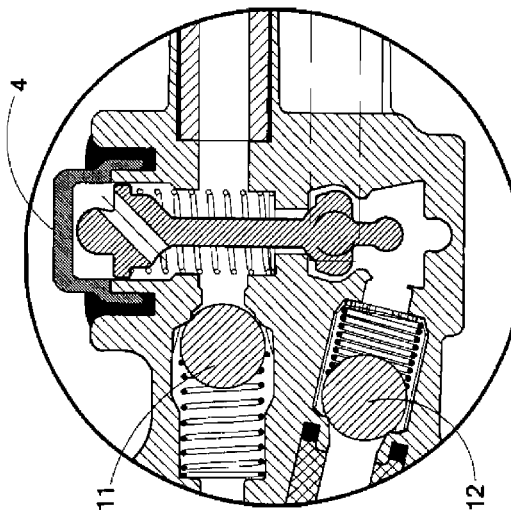
FIG. 10a is a sectional view of the pump with the illustrative one-touch release shown in FIG. 3, depicting an alternative ball and socket deflate valve in an inflate mode.
Figure 10B:
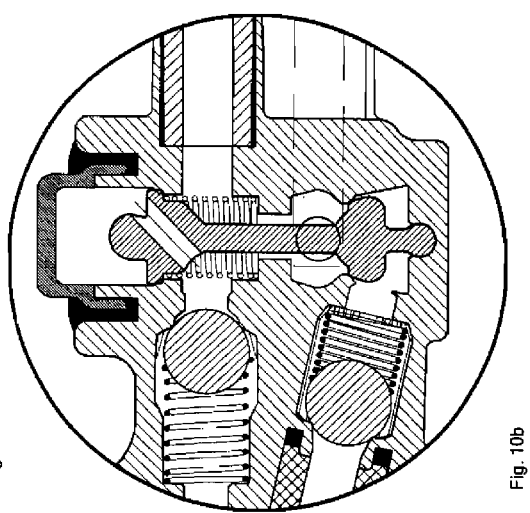
FIG. 10b is a sectional view of the pump with the illustrative one-touch release shown in FIG. 3, depicting an alternative ball and socket deflate valve in a deflate mode.

FIGS. 10a and 10b are sectional views of pump 3, depicting deflate valve 4 with an alternative ball and socket restriction means, in an inflate mode and a deflate mode, respectively. Specifically in these drawings, pump 3 includes inlet valve 11, exhaust valve 12 and deflate valve 4.

FIG. 10c is a sectional view of pump 3 with sub-assembly 301 removed. Deflate valve chamber 300 in FIG. 10c is similar to that in FIG. 8c, except that ball socket 347 is also incorporated into chamber floor 315.

FIG. 10d is an illustration of sub-assembly 301 of FIGS. 10a-b. Valve 302 in FIG. 10d is similar to that in FIG. 8d, except that stem 348 and ball 349 extend beyond valve base 342. Ball 349 engages socket 347 when valve 302 is in the deflate mode. Ball 349 and socket 347 cooperate to maintain valve 302 in the deflate mode either independently of, or in conjunction with, restriction means provided by interaction of valve ring engagement surface 341 and restriction ring 317. In either case, valve ring engagement surface 341 and restriction ring 317 can contact to form a fluid seal so that valve 302 can be moved by pressurization of actuator compartment 328 during subsequent inflation of the IPP.

FIGS. 11a and 11b are sectional views of pump 3, depicting an alternative articulated deflate valve 4 in an inflate mode and a deflate mode, respectively. In these drawings, depicted are inlet valve 11, exhaust valve 12, and alternative articulated deflate valve 4.

FIG. 11c is a sectional view of pump 3 with alternative articulated deflate valve sub-assembly 301 removed. FIG. 11c is for the most part identical to FIG. 8c.

FIG. 11d is an illustration of alternative articulated deflate valve 4 of FIGS. 11a-b. Therein depicted is deflate valve sub-assembly 301 with articulated valve 302, valve cap 322, and spring 303. FIG. 11d is similar to FIG. 8d except that an extra component, cap 322, slides on articulated valve 302. Bore 350 of cap 322 slides axially on valve extension 351 of valve 302, while counter bore 352 of cap 322 slides axially on radial surface 353 of valve 302. Valve extension 351 projects from valve base 342 and terminates with a tubular end 354 that is mechanically expanded to form cap retainer 355. Articulated valve 301 lengthens to provide a means to compensate for axial expansion of deflate chamber 300, so ring engagement surface 341 of cap 322 is retained in restriction ring 317.

Figure 12A:
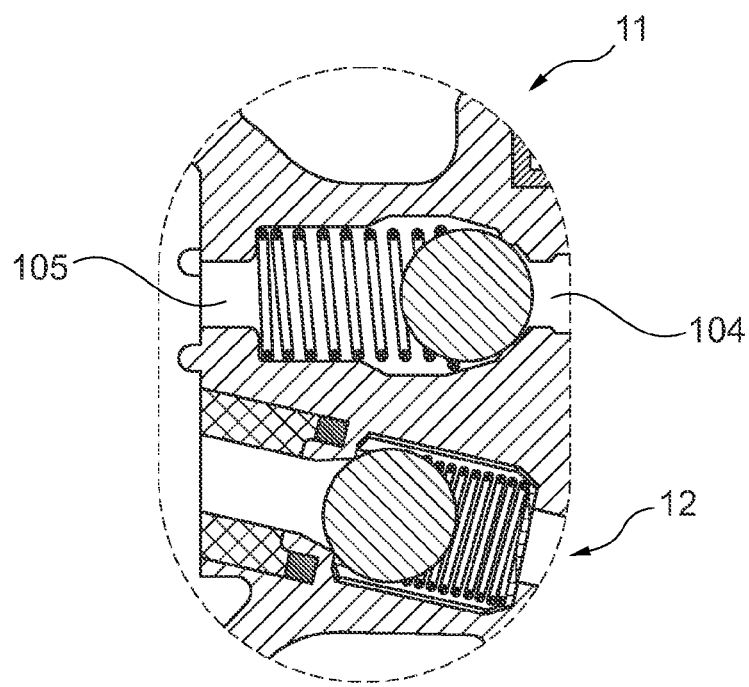
FIG. 12a is a sectional view of a single function inlet valve and exhaust valve assembly of the prior art.
Figure 12B:
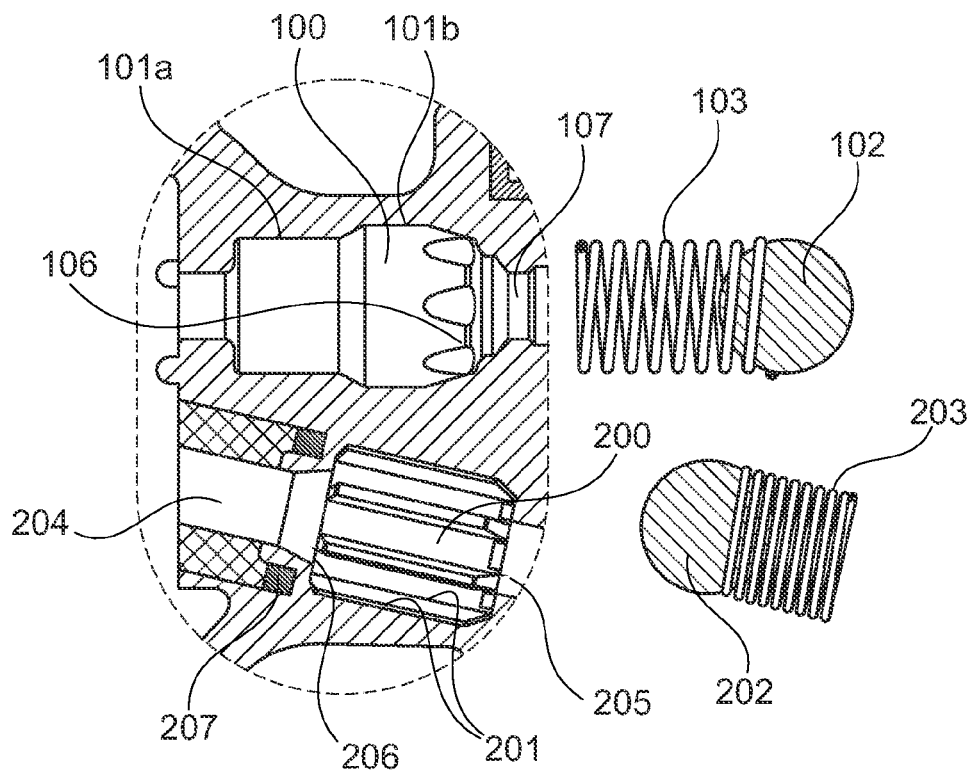
FIG. 12b is an illustration of the valve assembly of FIG. 12a with balls and springs removed therefrom.

FIGS. 12a and 12b are sectional views of a single function inlet valve assembly 11 and exhaust valve assembly 12 of the prior art. FIG. 12b, specifically, is an illustration of inlet valve assembly 11 and exhaust valve assembly 12 of FIG. 12a with balls and springs removed therefrom. FIGS. 12a-b show an inlet valve chamber 100, with internal surfaces 101a and 101b, which supports a spring 103 and a valve 102 respectively. Chamber 100 has an entry 104, an exit 105, an elastomeric valve seat 106, and a valve retainer 107 that may prevent valve 102 from jamming in elastomeric valve seat 106. Inlet valve 11 functions to prevent fluid flow during pump bulb compression and to open so that fluid can flow from reservoir 1 into pump bulb 8 as it rebounds.

FIGS. 12a-b also depict an exhaust valve assembly 12 that may include a valve chamber 200 with internal surfaces 201 that in turn support a valve 202 and a spring 203. Chamber 200 has an entrance 204, an exit 205, and an elastomeric valve seat 206. Elastomeric valve seat 206 is stabilized with a seat reinforcement 207 that prevents valve 202 from extruding through valve seat 206 at elevated cylinder pressures. Seat reinforcement 207 is configured as a ring and may be fabricated from any suitable material, such as an MP35N metal alloy, Polysulfone plastic, or a composite material of multiple polyester fibers and filaments that are radially wound in a polymer matrix such as a silicone elastomer. In certain implementations, a function of exhaust valve 12 is to allow fluid to flow from pump bulb 8 to cylinders 5a-b when pump bulb 8 is compressed. During rebound of pump bulb 8, exhaust valve 12 closes to prevent fluid backflow from cylinders 5a-b to pump bulb 8. Another function of exhaust valve 12 can be to provide pump backpressure resistance to prevent fluid flow from reservoir 1 to cylinders 5a-b through pump 3. Pump bulb resistance to compression increases as backpressure resistance is increased. In certain implementations, backpressure resistance may be limited to a range that permits comfortable compression of pump bulb 8 in the scrotum. Spring 203 is sized to provide backpressure resistance within a specified range.

Figure 12C:
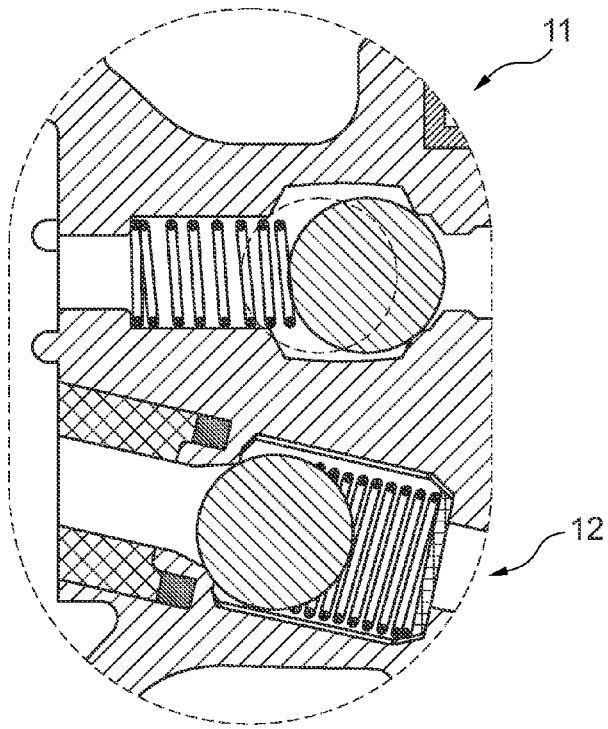
FIG. 12c is a sectional view of a multi-functional inlet valve with a secondary valve seat and an exhaust valve.
Figure 12D:
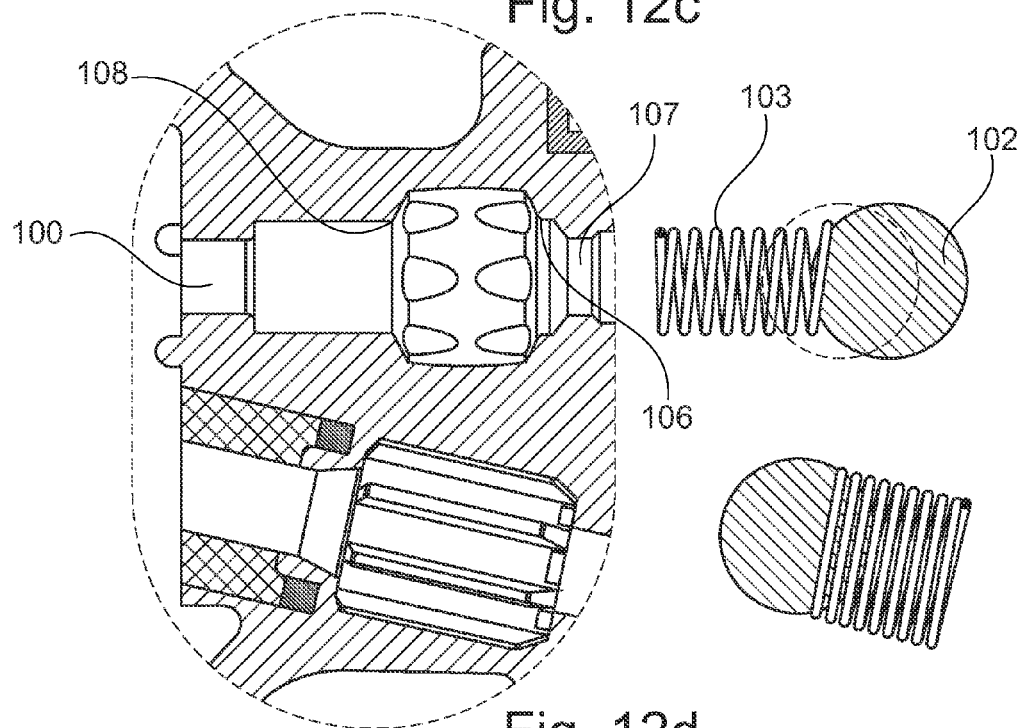
FIG. 12d is an illustration of the valve assembly of FIG. 12c with balls and springs removed therefrom.

FIGS. 12c and 12d are sectional views of a multi-functional inlet valve assembly 11 and exhaust valve assembly 12 with a secondary inlet valve seat 108 in assembly 11; and FIG. 12d, specifically, is an illustration of valve assemblies 11 and 12 of FIG. 12c with balls and springs removed therefrom as will be described. Valve chamber 100 includes a secondary valve seat 108 that prevents flow through inlet valve assembly 11 upon IPP deflation at elevated (e.g., 15-75 psi) penile cylinder pressures. In FIG. 12c, ball 102 is depicted as a solid line against valve seat 106 and as a hidden line against valve seat 108. Spring 107 is sized to prevent ball 102 from contacting valve seat 108 during rapid rebound of the pump bulb, but yet to allow ball 102 to close against valve seat 108 when fluid returns from the penile cylinders at a relatively high velocity. In certain implementations, one function of inlet valve assembly 11 is to prevent fluid flow during pump bulb compression, and to open so that fluid can flow from reservoir 1 into pump bulb 8 as it rebounds. A secondary function of inlet valve assembly 11 is to prevent fluid from pressurizing pump bulb 8 during IPP deflation at elevated penile cylinder pressures.

FIGS. 12e, 12f, and 12g are sectional views of a multi-functional inlet valve assembly 11 and exhaust valve assembly 12, with a secondary inlet valve seat 108 and a spring loaded dashpot-type inlet valve. FIG. 12f is an illustration of valve assemblies 11 and 12 in FIG. 12e with valve components removed therefrom. Inlet valve assembly 11 includes an inlet valve chamber 100 with internal surfaces 101. Valve chamber 100 includes a secondary valve seat 108 that prevents fluid flow through valve assembly 11 upon IPP deflation at elevated (e.g., 15-75 psi) penile cylinder pressures. Multi-functional inlet valve has a dashpot-type inlet valve that comprises a dashpot piston 109, dashpot spring 113, dashpot housing 110 and dashpot valve ball 111. Dashpot housing 110 cooperates with valve seat 106 as an inlet valve. Dashpot piston 109 cooperates with valve seat 108 as a pump lockout valve. Dashpot valve ball 111 cooperates with valve seat 112 as a dashpot valve. A bore of dashpot housing 110 cooperates with a major diameter of dashpot piston 109 to form a metered fluid pathway. Both are sized to allow fluid to return to an interior of the dashpot-type valve at a rate that can allow fluid to fill there within during a time period just slightly longer (e.g., one second) than is required for pump bulb 8 to rebound and fill with fluid. Dashpot valve ball 111 cooperates with valve seat 112, opening to empty the dashpot-type valve when pump bulb 8 is compressed and closing when pump bulb 8 rebounds to refill. During rebound of the pump bulb, dashpot piston 109 does not close against valve seat 108 until the dashpot-type valve refills and fully extends. The dashpot-type valve is refilled with fluid returning through a metered fluid pathway between the aforementioned bore of dashpot housing 110 and the major diameter of dashpot piston 109. As aforedescribed relative to FIGS. 12c-d, in certain implementations, one function of valve assembly 11 is to prevent fluid flow during pump bulb compression, and to open so that fluid can flow from reservoir 1 into pump bulb 8 as it rebounds. Another function of valve assembly 11 can be to prevent fluid from pressurizing pump bulb 8 during IPP deflation at elevated penile cylinder pressures. In this configuration, valve assembly 11 also acts as a pump lockout valve to prevent fluid flow from reservoir 1, through pump bulb 8, to the penile cylinders. FIG. 12g is an illustration of valve assemblies 11 and 12 in FIG. 12e with inlet valve assembly 11 being in an open position.

Figure 12H:
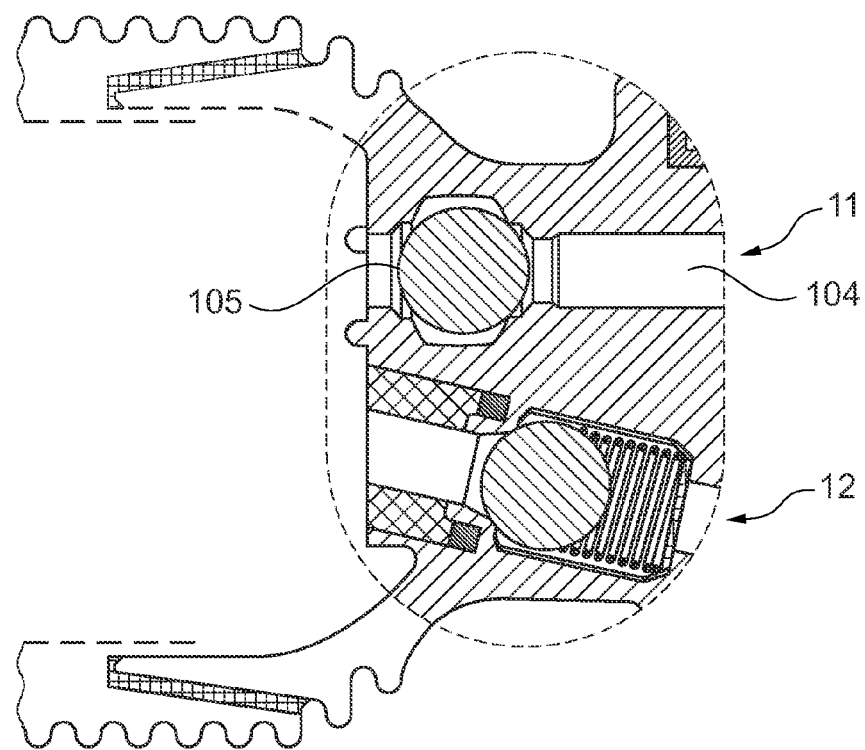
FIG. 12h is a sectional view of a multi-functional inlet valve with a secondary valve seat, located in proximity to the pump bulb to cause distortion of the secondary valve seat during pump bulb rebound, and an exhaust valve.
Figure 12J:
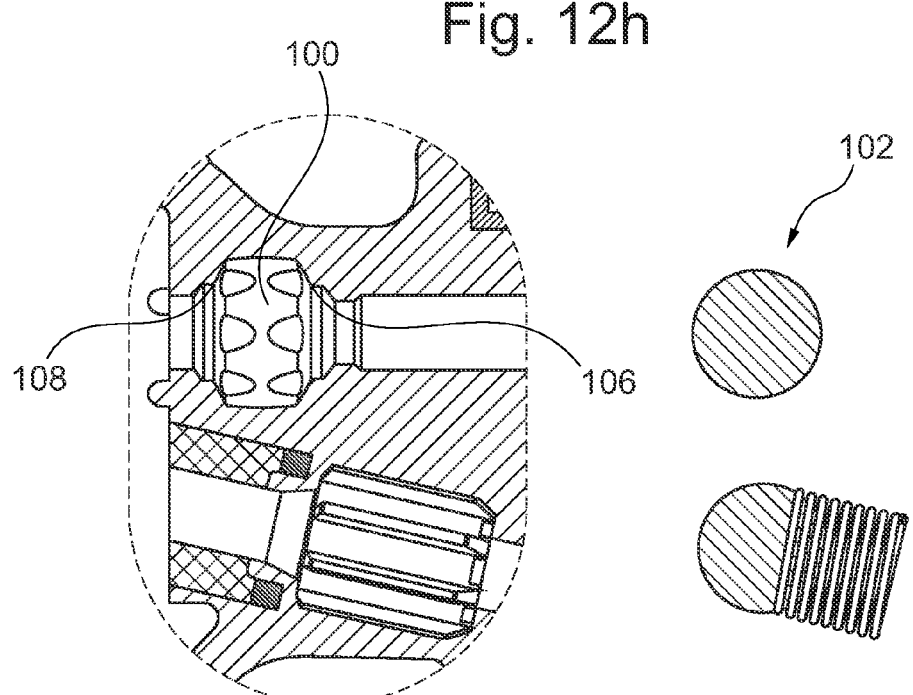
FIG. 12j is an illustration of the valve assembly of FIG. 12h with the valve components removed therefrom.

FIG. 12h is a sectional view of a multi-functional inlet valve assembly 11 and exhaust valve assembly 12, with a secondary inlet valve seat 108 located in proximity to pump bulb 8 to intentionally cause distortion of secondary inlet valve seat 108 during pump bulb rebound. FIG. 12j is an illustration of valve assemblies 11 and 12 of FIG. 12h with valve components removed therefrom. Valve assembly 11 includes a valve chamber 100 with internal surfaces that in turn support a valve ball 102. Valve chamber 100 includes a secondary valve seat 108 located in proximity to pump bulb 8. During pump bulb rebound, secondary valve seat 108 is distorted so that valve ball 102 does not seat and fluid from reservoir 1 can enter pump bulb 8. When pump bulb 8 fully rebounds, valve ball 102 closes against valve seat 108 to prevent fluid flow through valve assembly 11 during IPP deflation at elevated (e.g., 15-75 psi) cylinder pressures.

FIG. 13a is a magnified illustration of a clamshell-like girdle component 14 of pump 3, and FIG. 13b is a magnified illustration of a complimentary snap ring 15 to secure girdle component 14. Girdle component 14 and snap ring 15 may also (i) function to reinforce and stabilize elastomeric deflate chamber 300 (as aforedescribed in FIGS. 4a-7b), or (ii) function to reinforce and stabilize an entire valve segment of pump 3, or (iii) incorporate a different tactile characteristic in the valve segment of pump 3. Girdle component 14 may be molded plastic such as Polysulfone or a metal stamping such as stainless steel or MP35N. As depicted, clamshell-like girdle component 14 could be molded with separation 16 at least partially open and apart to facilitate the molding process and could be further opened for installation in the valve segment of pump 3. Girdle component 14 could also be formed in two halves with two snap rings or formed in two halves with integral latching mechanisms to secure them in place. Girdle component 14 intimately contacts pump 3 to reduce deformation thereunder in most directions.

Figure 14:
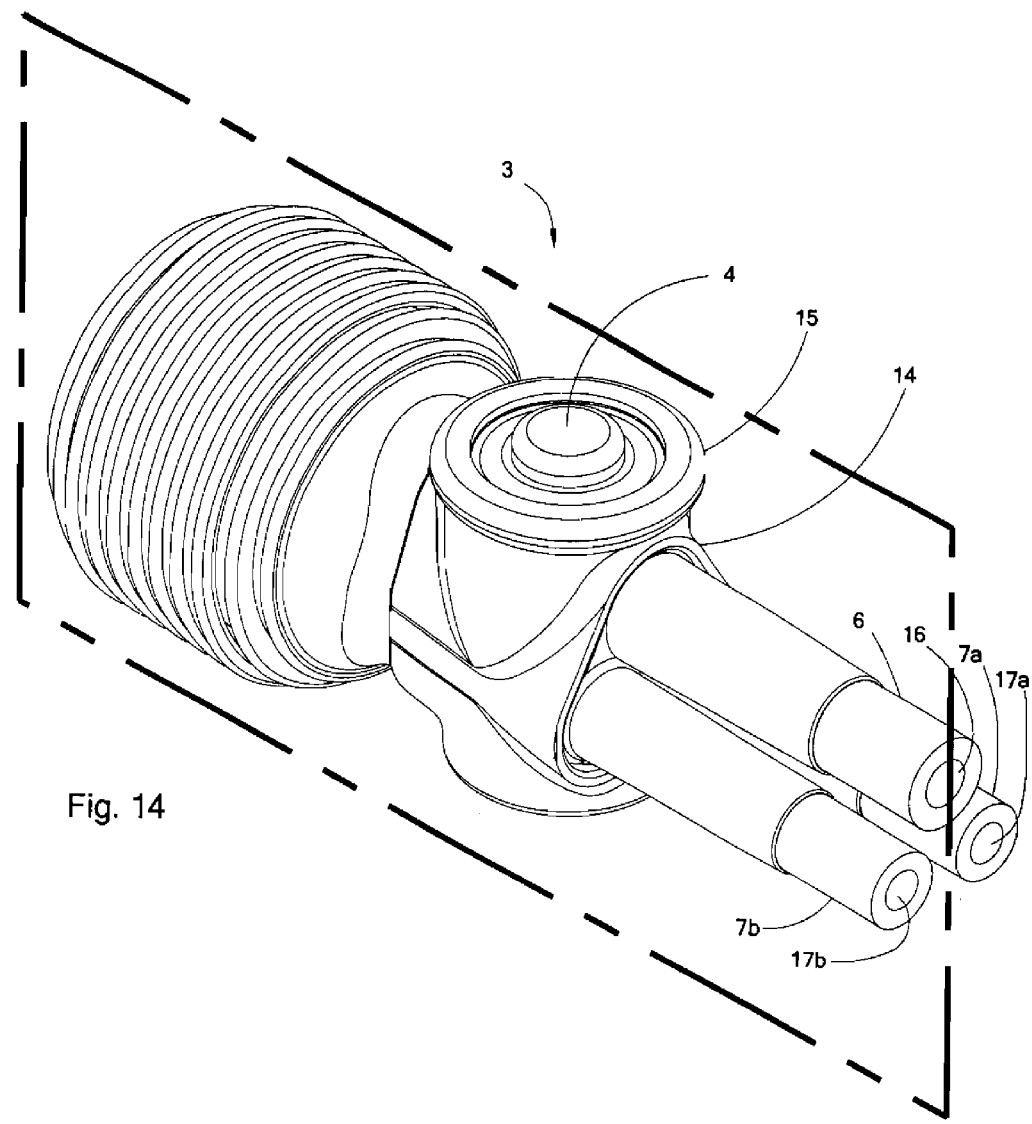
FIG. 14 is an illustration of an alternative embodiment of the pump with the illustrative one-touch release shown in FIG. 3 and utilizing an articulated deflate valve as shown in FIG. 11d, with an inlet conduit having a bore larger than those of either exhaust conduit leading to the penile cylinders.

FIG. 14 is an illustration of an alternative embodiment of pump 3 shown in FIG. 3 and utilizing an articulated deflate valve as shown in FIG. 11d, with inlet tubing having a bore larger than those of either exhaust tubing leading to the penile cylinders; commonly, the exhaust tubing can have identical bore dimensions. Bore 16 of inlet tubing 6 between pump 3 and reservoir 1 is greater than both (i) bore 17a of exhaust tubing 7a between pump 3 and penile cylinder 5a and (ii) bore 17b of exhaust tubing 7b between pump 3 and penile cylinder 5b. As aforedescribed, girdle component 14 with snap ring 15 are used to stabilize deflate valve chamber 300.

Figure 15E:
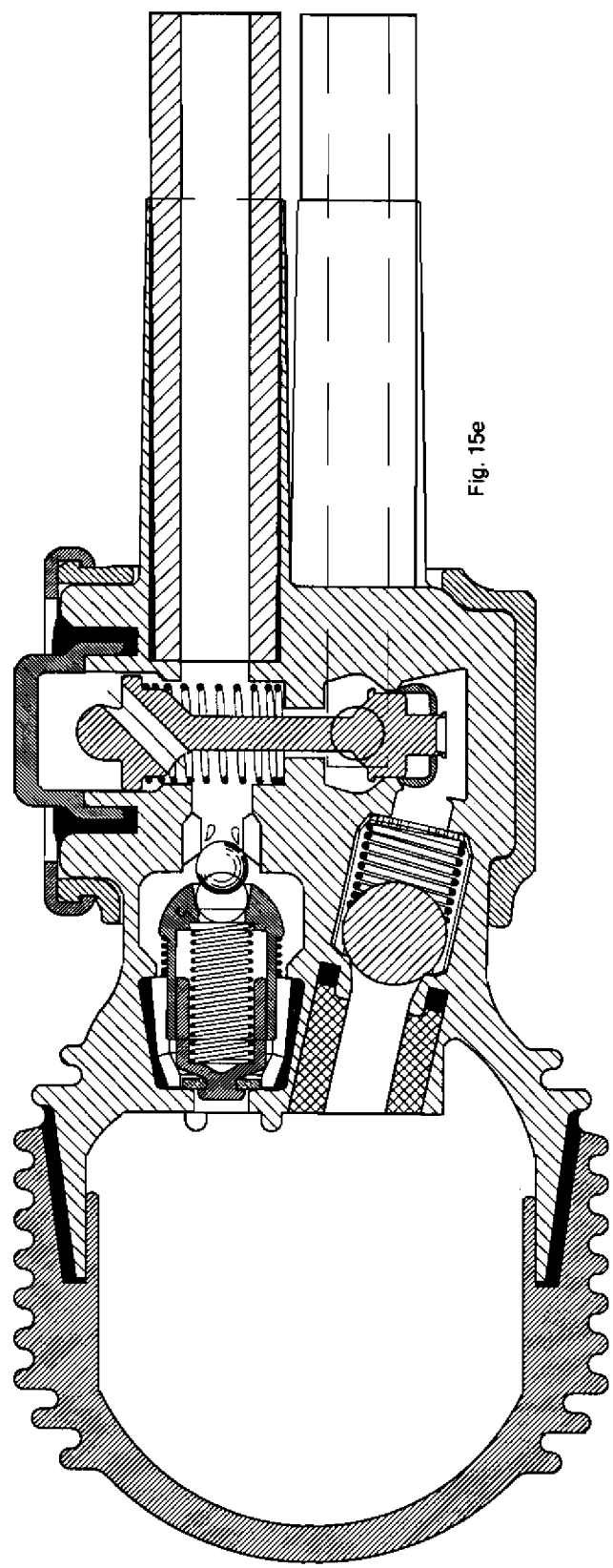
FIG. 15e is a sectional view of the alternative embodiment of the pump with the illustrative one-touch release shown in FIG. 14, after the deflate valve is activated and the fluid returns from the cylinders to the reservoir.

FIG. 15a through 15e are sectional views depicting another exemplary embodiment of pump 3 and deflate valve 4. Specifically, FIG. 15a is a sectional view of pump 3 when a penis within which the IPP is implanted is flaccid and the reservoir is filled. FIG. 15b is a sectional view of pump 3 when the pump bulb is squeezed and fluid flows into the penile cylinders. FIG. 15c is a sectional view of pump 3 when the pump bulb is released and fluid is drawn into the pump bulb from the reservoir. FIG. 15d is a sectional view of pump 3 when the penis is erect. FIG. 15e is a sectional view of pump 3 after the deflate valve is activated and the fluid returns from the cylinders to the reservoir.

In FIGS. 15a-e, with reference also to FIGS. 16a, 16b, 16c, 16d, and 16e, inlet valve 11 is a multi-functional dashpot-type lockout valve (like that shown in FIGS. 12e-g) that includes an elastomeric inlet valve chamber 100, an internally ported sleeve 114, a valve seal 115, a dashpot piston 109, an inlet valve spring 103, a dashpot spring 113, a dashpot housing 110, and a dashpot valve ball 111. Internally ported sleeve 114, dashpot piston 109, inlet valve spring 103, dashpot spring 113, dashpot housing 110, and dashpot valve ball 111 may each be preferably fabricated from a 35% nickel, 35% cobalt, 20% chromium, and 10% molybdenum alloy such as is available from SPS Technologies as trademark material MP35N, having a hardness of approximately 50 Rockwell C. Valve seal 115 may be fabricated from a 35-55 Shore A Durometer silicone elastomer. Exhaust valve 12 may serve as either a single-function check valve allowing one-way fluid flow from reservoir 1 to penile cylinders 5a-b via pump bulb 8, or as a multi-functional valve that can also prevent fluid flow from reservoir 1 to cylinders 5a-b via pump bulb 8 within a predetermined backpressure range. Exhaust valve 12 can consist of an elastomeric valve chamber 200, a valve ball 202, and a spring 203. Ball 202 and spring 203 may be fabricated from the aforementioned MP35N material.

Also in these FIGS. 15a-e and 16a-e, deflate valve 4 is a multi-functional valve having an elastomeric valve chamber 300, an elastomeric deflate cap 13, a coil spring 303, and an articulated valve sub-assembly 301 that in turn includes a deflate valve 302, a deflate valve spring 303, and a deflate valve cap 322. These components may be preferably fabricated from the aforementioned MP35N material; but the cap can be fabricated from Udel P-1700 series Polysulfone.

Again in FIG. 15a, exhaust valve 12 and deflate valve 4 are depicted when the penis is flaccid and reservoir 1 is filled. Therein, articulated valve sub-assembly 301 is open; and the dashpot-type inlet valve with lockout 116 and exhaust valve 202 are both closed. With reference to FIGS. 16a, 16b, and 16c, lockout 116 comprises a valve seat, valve seal, and dashpot piston.

FIG. 15b is a sectional view of the alternative embodiment of pump 3 as shown in FIG. 14, including inlet valve 11, exhaust valve 12, and deflate valve 4, when pump bulb 8 is squeezed and fluid flows into penile cylinders 5a-b. In this condition, dashpot valve 111, lockout valve 116, and exhaust valve 202 are open, while inlet valve 102 and deflate valve 301 are closed.

FIG. 15c is a sectional view of the alternative embodiment of pump 3 as shown in FIG. 14, including inlet valve 11, exhaust valve 12, and deflate valve 4, when pump bulb 8 is released and rebounds, and fluid is drawn thereinto from reservoir 1. In this condition, inlet valve 102 and lockout valve 116 are open, while dashpot valve 111, exhaust valve 202, and deflate valve 301 are closed.

FIG. 15d is a sectional view of the alternative embodiment of pump 3 as shown in FIG. 14 when the penis is erect, including inlet valve 11, exhaust valve 12, and deflate valve 4. In the condition depicted, dashpot valve 111, inlet valve 102, lockout valve 116, exhaust valve 202, and deflate valve 301 are closed.

FIG. 15e is a sectional view of the alternative embodiment of pump 3 as shown in FIG. 14, including inlet valve 11, exhaust valve 12, and deflate valve 4. The condition depicted is after deflate valve 4 is activated and fluid returns from cylinders 5a-b to reservoir 1. Therein, inlet valve 102 and deflate valve 301 are open, while lockout valve 116 and exhaust valve 202 are closed. Dashpot valve 111 opens then closes.

FIG. 16a is an illustration of the alternative embodiment of the pump with a one-touch release of FIGS. 15a-e, with inlet and pump lockout valve components removed therefrom. As depicted therein, inlet valve chamber 100 has inlet valve seat 106 penetrating end surface 117, lockout valve seat 108 penetrating end surface 118, frusto-conical surface 119 that is configured to fit external surface 120 of internally ported sleeve 114, radial surfaces 121 and 122, and frusto-conical surfaces 123.

FIG. 16b depicts inlet and pump lockout valve components as a sub-assembly. This sub-assembly incorporates a dashpot that serves as a time delay to keep lockout valve 116 open during rebound of pump bulb 8. A time delay for this configuration in its operation is about 2 to 4 seconds, depending on time required to refill pump bulb 8. A gap between bore 124 of dash pot housing 110 and major diameter 125 of dash pot piston 109, is sized to meter fluid flow into the dash pot so that lockout valve seal 115 is kept away from valve seat 108 while pump bulb 8 rebounds and fills with fluid from reservoir 1. Except for elastomeric seal 115, the inlet and pump lockout valve components can be fabricated from the aforementioned MP35N material.

FIG. 16c is an exploded illustration of the valve component shown in FIG. 16b. Therein depicted, from left to right, are: internally ported sleeve 114, lockout valve seal 115, dash pot piston 109, inlet valve spring 103, dash pot spring 113, dash pot housing 110 and dash pot valve ball 111. Internally ported sleeve 114 has fluid channels 126 for fluid flow around dash pot piston 109 and dash pot housing 110. Lockout valve seal 115 is an optional elastomeric seal. Seal 115 has opposed surfaces that seal with both valve seat 108 and dashpot piston 109. Seal 115, which may appear to be unnecessary, was added to accommodate distortions which may occur in elastomeric valve seat 108 while maintaining a seal with a more rigid dash pot piston 109.

FIG. 16d depicts exhaust valve components as shown in FIGS. 15a-e.

FIG. 16e depicts the deflate valve subassembly as shown in FIGS. 15a-e.

With reference again to FIGS. 16b-c, dash pot piston 109 has a frusto-conical sealing surface 127, a button head 128 for retaining seal 115, a major diameter 125 that cooperates with counter-bore 124 of dash pot housing 110 to meter fluid flow, and a recess 129 that houses dash pot spring 113. Inlet valve spring 103 is, as shown, can include a coil-type compression spring that acts upon dash pot housing 110 to bias it against inlet valve seat 106. Dash pot spring 113 is, as shown, can include a coil-type compression spring that is biased to separate dash pot piston 109 and dash pot housing 110. Dash pot housing 110 has a counter-bore 124 that cooperates with major diameter 125 of piston 109 to meter fluid flow. An external cylindrical surface 130 supports inlet valve spring 103. Spherical valve surface 131 forms inlet valve 102 that cooperates with inlet valve seat 106 as shown in FIG. 16a. An aperture 132 penetrates spherical surface 131 and contains dash pot valve seat 112 that cooperates with a dash pot ball 111. Dash pot ball 111, in turn, cooperates with valve seat 112 of dash pot housing 110 to serve as a dash pot valve that permits fluid to be expelled therefrom and prevents fluid from entering when dashpot piston 109 is separating from dash pot housing 110.

The above described implementations may include the following features and functions:

I. A pump with a one-touch release constructed can function so that a device fluidly connected therewith may be easily and quickly deflated by an initial, nearly instantaneous activation rather than by requiring sustained pressure thereon or prolonged activation thereof.

II. A pump of includes of a pump bulb and a valve segment, with tubing or fluid conduits connecting the pump bulb with the valve segment, and tubing or fluid conduits connecting the valve segment with a reservoir and at least one penile cylinder.

III. A one-touch release, bypass-type, multi-functional deflate valve can be located between pump inlet and exhaust fluid tubing or conduits leading to the reservoir and the penile cylinder.

IV. A larger bore tube or conduit between the pump and reservoir reduces time needed to inflate and deflate the IPP.

V. In certain implementations, a deflate valve is a multi-functional valve that prevents flow to the reservoir during cylinder inflation and provides backpressure resistance to flow from the reservoir when the cylinders have deflated. They are voluntarily or manually placed in a deflate mode, to drain fluid from the penile cylinder back to the reservoir. They are placed in the inflate mode with an initial collapsing of the pump bulb during subsequent cylinder inflation.

VI. Because the deflate valve provides a fluid conduit between the reservoir and cylinder, it may have backpressure resistance to resist autoinflation of the penile cylinder. The backpressure resistance can equal or exceed the backpressure resistance of the exhaust valve, in certain implementations, if neither a pump lockout valve nor a reservoir lockout valve are incorporated in the system. The backpressure resistance of the deflate valve can be greater than the exhaust valve because it is opened with a direct finger force on a small area rather than the fluid force generated by collapsing the larger pump bulb.

VII. The valve body may be an elastomeric chamber or an elastomeric insert within a less elastic metal or plastic valve body. The deflate valve is held in the deflate mode by an elastomeric restriction ring that is smaller than the deflate valve. The deflate valve and restriction ring cooperate to form a secondary valve that prevents fluid flow until the valve is moved from the deflate mode to the inflate mode. Fluid to move the deflate valve is delivered from the pump exhaust valve when it opens to expel fluid from the pump bulb as it is collapsed during device inflation.

VIII. In the inflate mode, the deflate valve cooperates with a primary valve seat to prevent fluid flow to the reservoir, resulting in cylinder inflation. Also, in the inflate mode, the deflate valve prevents the flow of fluid from the reservoir to the penile cylinders through the deflate valve, within the backpressure resistance of the deflate valve. The deflate valve is biased to maintain the inflate mode by a spring. The backpressure resistance can be adjusted by varying the spring force.

IX. Based on experience in patients, it is believed that an IPP pump can operate at pressures up to 75 psi. Fluid returning from two fluid tubes or conduits emanating from two penile cylinders can ultimately flow through a single tube or conduit leading to the reservoir. If such fluid conduits have a similar bore and the pump is placed in the deflate mode at elevated pressures, in the range of 15-75 psi, the fluid velocity can open the inlet valve and pressurize the pump bulb. If the intraluminal pressure in the pump bulb exceeds the exhaust valve backpressure, the exhaust valve can open and the flow of fluid may place the deflate valve in the inflate mode before device deflation is accomplished. To mitigate these phenomena from occurring at high pressure excursions, the pump inlet valve can also be multi-functional.

X. The pump inlet valve is minimally biased in the closed position so that it can open to allow fluid flow from the reservoir to the pump bulb as the pump bulb rebounds. Pump bulb rebound causes a small negative pressure on the inlet valve, usually less than 10 inches of mercury. The inlet valve can open fully at negative pressures less than 10 inches of mercury. Previously, inlet valves did not require multi-functional capability. With the potential for high pressure excursions and the placement of the deflate valve between the inlet valve and reservoir, the inlet valve can close during high pressure excursions. Conversely, the valve may not close during normal low pressure operation, or it may prevent fluid flow from the reservoir to the pump bulb.

XI. The inlet valve cooperates with the primary valve seat to prevent fluid from returning to the reservoir when the pump bulb is collapsed. There are several ways to incorporate multi-functional capability into the inlet valve:

1. The primary inlet valve could cooperate with a secondary valve seat to prevent flow from the deflate valve to the pump bulb. The inlet valve spring can be sized so that the inlet valve remains open at low pressure and closes at elevated pressure.

2. The primary inlet valve could be reconfigured so that it remains open for a few seconds after the pump bulb is collapsed to allow the pump bulb to rebound and refill before closing. This requires a valve that shortens, then elongates within a few seconds time. A spring-loaded dashpot-type valve can shorten when a pressure differential opens the valve. The valve can extend and close against the primary valve seat, as fluid is metered into the valve dashpot to allow valve expansion.

3. The inlet valve, having a secondary valve seat that is located where it can be distorted during pump bulb rebound, provides a fluid flow from the reservoir during pump bulb rebound and otherwise remains in the closed position.

XII. The deflate valve can use an elastomeric restriction ring to engage the deflate valve and maintain it in the deflate mode as it is voluntarily or manually shifted. In one version, a ball on the end of the valve engages an elastic socket in the secondary valve chamber to augment or replace the restriction ring in maintaining the deflate valve in the deflate mode. With the ball and socket, the restriction ring still cooperates with the deflate valve to form a second valve that restricts fluid flow, causing the deflate valve to change to the inflate mode when the pump bulb is collapsed.

XIII. Initial development began with an elastomeric deflate valve test block and progressed to a complete pump assembly incorporating the deflate valve.

XIV. The requirement for deflate valve backpressure resistance resulted in four distinct spring designs that were considered.
1. Compression-type coil spring.
2. Plastic rim with spokes.
3. Elastomeric disc with apertures.
4. Plastic or metal radial finger spring.

The valve designs were essentially the same with four variations prototyped.
1. Plain.
2. Elongated ring engagement surface.
3. Ball and socket.
4. Articulated.

XV. An unsupported elastomeric deflate valve chamber increases radially and axially with intraluminal pressurization. Several means were identified to mitigate the adverse effect of pressure deformation of the deflate valve chambers:
1. An elastomeric cylindrical insert with greater stiffness may be inserted inside the elastomeric valve segment. This could be accomplished with a higher durometer elastomer or by adding fillers or fiber reinforcement to the elastomer. The downside is bonding a sleeve with apertures corresponding to the fluid conduits terminating in the deflate chamber.
2. Add a plastic girdle around the pump exterior in the area of the deflate valve to limit both radial and axial deformation.
3. Radial deformation of the restriction ring may be mitigated by decreasing the diameter of the ring so it engages the deflate valve even when the ring is expanded. The downside is that deflate valve can be more difficult to return to the inflate mode when the device is deflated and the ring is not expanded.
4. Axial deformation may be mitigated with a valve having an elongated ring engagement or with an articulated valve that increases in length with axial deformation.

XVI. Finally, and with continued reference to all of the drawings, operation of various combinations of aforedescribed features and embodiments can include:

1. Inlet, Exhaust, and Deflate Valves—Sequence of Operations.
  1A. Penis is flaccid; reservoir is filled.
    Inlet valve is closed;
    Exhaust valve is closed; and
    Deflate valve is closed.
  1B. Pump Bulb is squeezed.
    Inlet valve is closed;
    Exhaust valve is opened to allow fluid flow and is biased to close, ceasing flow;
    Deflate valve is closed and remains closed during subsequent pump bulb activation; and
    Fluid flows from pump bulb through exhaust valve, to penile cylinder(s).
  1C. Pump Bulb is released.
    Fluid is drawn from reservoir through inlet valve, to pump bulb;
    Inlet valve is opened to allow fluid flow and is biased to close when flow ceases;
    Exhaust valve is closed; and
    Deflate valve is closed.
  1D. Penis is erect; penile cylinder(s) is(are) filled.
    Inlet valve is closed;
    Exhaust valve is closed; and
    Deflate valve is closed.
  1E. Deflate valve is activated.
    Fluid flows from penile cylinder(s) through deflate valve, to reservoir;
    Inlet valve is closed;
    Exhaust valve is closed; and
    Deflate valve is opened.

2. Inlet, Exhaust, Pump Lockout, and Deflate Valves—Sequence of Operations.
  2A. Penis is flaccid; reservoir is filled.
    Inlet valve is closed;
    Exhaust valve is closed;
    Deflate valve is closed; and
    Pump lockout valve is closed.
  2B. Pump Bulb is squeezed.
    Inlet valve is closed;
    Exhaust valve is opened to allow fluid flow and is biased to close, ceasing flow;
    Deflate valve is closed and remains closed during subsequent pump bulb activation;
    Fluid flows from pump bulb through exhaust valve, to penile cylinder(s); and
    Pump lockout valve is opened.
  2C. Pump Bulb is released.
    Fluid is drawn from reservoir through inlet valve, to pump bulb;
    Inlet valve is opened to allow fluid flow and is biased to close when flow ceases;
    Exhaust valve is closed;
    Deflate valve is closed; and
    Pump lockout valve is opened to allow fluid flow, and is biased to close within a predetermined time after fluid flow ceases.
  2D. Penis is erect; penile cylinder(s) is(are) filled.
    Inlet valve is closed;
    Exhaust valve is closed;
    Deflate valve is closed; and
    Pump lockout valve is closed.
  2E. Deflate valve is activated.
    Fluid flows from penile cylinder(s) through deflate valve, to reservoir;
    Inlet valve is closed;
    Exhaust valve is closed;

Deflate valve is opened; and
Pump lockout valve is closed.
3. Inlet, Exhaust, and Pump Lockout Valves—Sequence of Operations.
3A. Penis is flaccid; reservoir is filled.
Inlet valve is closed;
Exhaust valve is closed; and
Pump lockout valve is closed.
3B. Pump Bulb is squeezed.
Inlet valve is closed;
Exhaust valve is opened to allow fluid flow and is biased to close, ceasing flow;
Pump lockout valve is opened; and
Fluid flows from pump bulb through exhaust valve, to penile cylinder(s).
3C. Pump Bulb is released.
Fluid is drawn from reservoir through inlet valve, to pump bulb;
Inlet valve is opened to allow fluid flow and is biased to close when flow ceases;
Exhaust valve is closed; and
Pump lockout valve is opened to allow fluid flow, and is biased to close within a predetermined time after fluid flow ceases.
3D. Penis is erect; penile cylinder(s) is(are) filled.
Inlet valve is closed;
Exhaust valve is closed; and
Pump lockout valve is closed.
3E. Deflation is activated.
Fluid flows from penile cylinder(s) through an open exhaust valve, then through an open pump lockout valve, and then through an open inlet valve to the reservoir.

Although certain implementations have been particularly shown and described with reference to the accompanying figures and specification, it will be understood however that other modifications thereto are of course possible; and all of which are intended to be within the true spirit and scope of the present invention. It should be appreciated that components, dimensions, elapsed times, and other particulars of exemplary embodiments aforedescribed may be substituted for others which are suitable for achieving desired results, or that various accessories may be added thereto. It is also to be understood in general that any suitable alternatives may be employed to provide the topical skin barriers and their evaluation methods.

It is to be noted that terms used here throughout are intended to have their usual, customary, and ordinary meanings, unless another is specified. That is, unless otherwise defined, all technical and scientific terms used herein have the same meaning as commonly understood by one of ordinary skill in the art to which this invention pertains. Although methods and materials similar or equivalent to those described herein can be used in the described implementations, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Although described in terms of utilization in IPPs, it is to be understood that the pump with a one-touch release could, of course, be utilized in any suitable application or environment where it would be desirable to provide such one-touch functionality.

Lastly, of course, the choice of compositions, sizes, and strengths of various aforementioned elements of exemplary implementations are a matter of design choice depending upon intended uses thereof.

Accordingly, these and other various changes or modifications in form and detail of the present invention may also be made therein, again without departing from the true spirit and scope of the invention as defined by the appended claims.

What is claimed is:

1. A pump adapted to be attached between a reservoir and an inflatable penile implant of an implantable penile prosthesis, the pump comprising:
   a pump body connected between a pump bulb and tubing that is attachable to the reservoir and to the inflatable penile implant;
   an inlet valve disposed within the pump body between the pump bulb and the tubing;
   an exhaust valve disposed within the pump body between the pump bulb and the tubing;
   a deflate valve disposed within the pump body between the inlet valve and the tubing, the deflate valve including a valve stem connected between a spring stabilizer and a valve surface;
   wherein the spring stabilizer is connected to a valve guide that is associated with a first end of the deflate valve;
   wherein the valve surface is connected to a valve shoulder that is associated with a second end of the deflate valve that is located opposite from the first end; and
   wherein an aperture is formed to extend entirely through the deflate valve.

2. The pump of claim 1, wherein the aperture is formed to extend through the valve guide.

3. The pump of claim 1, wherein the valve guide is wider than the spring stabilizer.

4. The pump of claim 1, wherein the valve shoulder is wider than the valve surface.

5. The pump of claim 1, further comprising a ring engagement surface connected between the valve shoulder and the second end of the deflate valve;
   wherein the guide surface and the ring engagement surface are equally wide relative to the valve stem.

6. The pump of claim 5, wherein the ring engagement surface is wider than the valve shoulder and wider than the valve surface.

7. The pump of claim 5, wherein the pump body includes a deflate valve chamber communicating with an actuator chamber, with the actuator chamber forming a restriction ring that is sized to engage the ring engagement surface of the deflate valve.

8. The pump of claim 1, wherein the first end of the deflate valve is curved and the second end of the deflate valve is flat.

9. The pump of claim 1, wherein the deflate valve is disposed within the pump body between the inlet valve and the tubing and between the exhaust valve and the tubing.

10. The pump of claim 1, wherein the deflate valve is disposed within the pump body transverse relative to the inlet valve.

11. The pump of claim 1, wherein the deflate valve is disposed within the pump body transverse relative to a flow path between the pump bulb and the reservoir.

12. The pump of claim 1, wherein the deflate valve is longer than the deflate valve is wide.

13. The pump of claim 1, further comprising a cap coupled to the second end of the deflate valve.

* * * * *